United States Patent [19]

Schulenberg

[11] 3,960,886

[45] June 1, 1976

[54] SUBSTITUTED N-ARYLANILINES

[75] Inventor: John W. Schulenberg, Bethlehem, N.Y.

[73] Assignee: Sterling Drug Inc., New York, N.Y.

[22] Filed: Nov. 20, 1970

[21] Appl. No.: 91,515

Related U.S. Application Data

[62] Division of Ser. No. 742,161, July 3, 1968, Pat. No. 3,625,972.

[52] U.S. Cl. ................... 260/326.5 L; 260/239 B; 260/239 BF; 260/247.2 A; 260/247.5 R; 260/268 R; 260/268 PH; 260/268 H; 260/293.69; 260/293.77; 260/293.79; 260/570.7; 424/248; 424/250; 424/267; 424/274

[51] Int. Cl.$^2$ ..................................... C07D 295/12

[58] Field of Search ............... 260/247.5 R, 268 R, 260/293.79, 296 AE, 326.5 L, 570.7, 268 PH, 239 B

[56] References Cited

UNITED STATES PATENTS

3,330,831   7/1967   English et al. ................... 260/268

FOREIGN PATENTS OR APPLICATIONS

1,302,373   7/1962   France ........................ 260/293.79

*Primary Examiner*—G. Thomas Todd
*Attorney, Agent, or Firm*—Thomas L. Johnson; B. Woodrow Wyatt

[57] ABSTRACT

N-Arylanilines, further substituted on nitrogen by aroyl, aralkanoyl or aralkyl groups, and wherein one of the aryl groups has a 3- or 4-(aminoalkoxy)substituent, having hypocholesteremic activity, are prepared by a series of O-alkylation, N-acylation or -alkylation, and reduction reactions starting from the appropriate hydroxydiarylamines or benzyl ethers thereof.

5 Claims, No Drawings

SUBSTITUTED N-ARYLANILINES

This application is a division of application Ser. No. 742,161, filed July 3, 1968, now U.S. Pat. No. 3,625,972.

This invention relates to substituted aniline derivatives and their preparation, and in particular is concerned with N-arylanilines further substituted on nitrogen by aroyl, aralkanoyl or aralkyl groups, and wherein one of the aryl groups has a 3- or 4-(aminoalkoxy)substituent. The invention is also concerned with processes for the preparation of the foregoing compounds and intermediates in said preparation.

The compounds of the invention have the following general formulas:

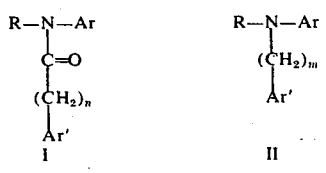

wherein R is phenyl or pyridyl; $n$ is 0 or an integer from 1 to 3; $m$ is an integer from 1 to 4; Ar and Ar' are phenyl, one of which is substituted in the meta or para position by the grouping —O—Y—N=Z, wherein Y is lower-alkylene and —N=Z is $NH_2$ or a basic secondary- or tertiary-amino group having a molecular weight less than about 200; and wherein the phenyl rings of R, Ar and Ar' can be further substituted by from one to three groups selected from the group consisting of lower-alkyl, lower-alkoxy, halogen (including fluoro, chloro, bromo or iodo), nitro and amino.

In the compounds of the invention wherein R is pyridyl, the pyridyl group is attached to the remainder of the molecule through a carbon atom of the pyridine ring. Thus, R can be 2-pyridyl, 3-pyridyl or 4-pyridyl.

In the side-chain, —O—Y—N=Z, attached to one of the aryl groups Ar and Ar', the lower-alkylene bridge, Y, stands for an alkylene radical of at least two and not more than five carbon atoms, thus including such radicals as —$CH_2CH_2$—, —$CH_2CH_2CH_2$—, —$CH(CH_3)CH_2$—, —$CH(CH_3)CH(CH_3)$—, —$CH_2CH_2CH_2CH_2$—, —$CH_2CH_2CH_2CH_2CH_2$—, and the like.

The terminal amino group, N=Z, stands for $NH_2$ or a basic secondary- or tertiary-amino group having a molecular weight less than about 200. The terms "secondary-amino" and "tertiary-amino" define radicals of the type —NHT and —NTT', respectively, wherein T and T' are organic radicals, so that the complete molecule containing the radical —NHT or —NTT' is a secondary- or tertiary-amine. Basic secondary- or tertiary-amino radicals are those of the aliphatic or araliphatic type that impart to the molecules which contain them sufficient basicity (ionization to the extent of at least $10^{-6}$) so that the compounds readily form acid-addition salts with strong inorganic and organic acids. A particularly preferred group of secondary- and tertiary-amino radicals are lower-alkylamino, for example, methylamino, ethylamino, butylamino, and the like; cycloalkylamino in which the cycloalkyl has from 5 to 6 ring members and a total of from five to about nine carbon atoms, for example, cyclopentylamino, cyclohexylamino, 4-methylcyclohexylamino, and the like; di-lower-alkylamino, for example, dimethylamino, diethylamino, dibutylamino, methylethylamino, and the like; dicycloalkylamino in which the cycloalkyl has from 5 to 6 ring members and a total of from five to about nine carbon atoms, for example, dicyclopentylamino, dicyclohexylamino, bis(4-methylcyclohexyl)amino, and the like; N-(cycloalkyl)-lower-alkylamino in which the cycloalkyl has from 5 to 6 ring members and a total of from five to about nine carbon atoms, for example, N-(cyclohexyl)methylamino, N-(cyclopentyl)ethylamino, and the like; polymethylenimino having from 5 to 7 ring members and a total of from four to about nine carbon atoms, for example, 1-pyrrolidyl, 1-piperidyl, hexamethylenimino and lower-alkylated derivatives thereof; 4-morpholinyl and lower-alkylated derivatives thereof; 1-piperazinyl and lower-alkylated derivatives thereof; 4-phenyl-1-piperazinyl; di-(phenyl-lower-alkyl)amino, for example, dibenzylamino, bis(phenylethyl)amino, and the like; and N-(phenyl-lower-alkyl)-lower-alkylamino, for example, N-(benzyl)methylamino, N-(phenylethyl)ethylamino, and the like. In the foregoing radicals, the term lower-alkyl stands for alkyl groups containing from one to about six carbon atoms.

In the event there are lower-alkyl, lower-alkoxy, or lower-alkylthio groups on the phenyl ring, the lower-alkyl moieties thereof have from one to four carbon atoms.

The compounds of formulas I and II wherein the side-chain O—Y—N=Z is attached to the meta or para position of the group Ar are prepared according to the following flow sheet:

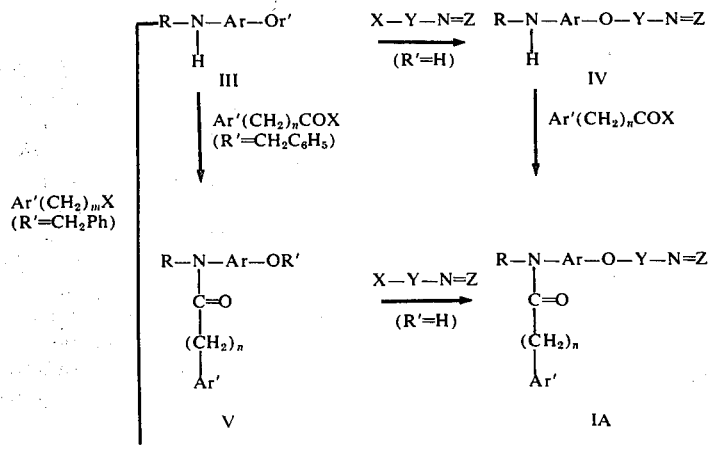

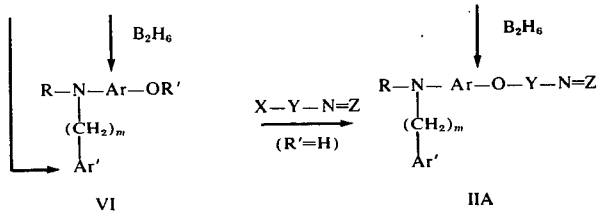

The starting material is an N-phenyl or N-pyridylhydroxyaniline (I, R'=H) or the benzyl ether thereof (I, R'=CH₂Ph). The former interacts with an amino-lower-alkyl halide, X—Y—N=Z (X=halogen, preferably chlorine or bromine), to give a basic ether of formula IV. The compound of formula IV is then acylated with an aroyl halide or aralkanoyl halide, Ar'(CH₂)ₙCOX, to give a compound of formula I where the side-chain —O—Y—N=Z is attached to the meta or para position of the group Ar (IA). The amide IA can then be reduced, preferably with diborane, to give a compound of formula II where the side-chain —O—Y—N=Z is attached to the meta or para position of the group Ar (IIA).

Alternatively, a compound of formula I wherein R' is benzyl is interacted with an aroyl halide or aralkanoyl halide, Ar'(CH₂)ₙCOX, to give a compound of formula V, wherein R' is benzyl, which in turn can be reduced with diborane to a compound of formula VI wherein R' is benzyl. A compound of formula VI, wherein R' is benzyl, can also be formed directly by alkylation of a compound of formula I, wherein R' is benzyl, with an aralkyl halide, Ar'(CH₂)ₘX. The compounds of formulas V and VI wherein R' is hydrogen, formed by hydrogenolysis of the compounds of formulas V and VI wherein R' is benzyl, are then interacted with an amino-lower-alkyl halide, X—Y—N=Z, to produce a compound of formula IA or IIA, respectively.

The O-alkylation reactions (III → IV, V → IA, and VI → IIA), and the N-acylation and N-alkylation reactions are carried out in an inert organic solvent in the presence of a base at a temperature between about 50° and 150°C. The base can be any strong base such as an alkali metal alkoxide, amide or hydride, or in the case of the N-acylation, an alkali metal carbonate.

The hydroboration reaction is conducted by contacting the N-acyl compound with diborane (B₂H₆) in an inert solvent such as tetrahydrofuran at a temperature between about 0° and 75°C.

The compounds of formulas I and II where the phenyl rings bear one or more amino (NH₂) groups are prepared by catalytic reduction of the corresponding nitro compounds.

The compounds of the invention wherein in the basic side-chain, O—Y—N=Z, the terminal amino moiety is primary-amino (NH₂) or secondary-amino are prepared by catalytic hydrogenolysis of the corresponding compounds wherein N=Z is dibenzylamino or N-benzyl-N-R''-amino, wherein R'' is the N-substituent desired in the secondary-amine, for example, lower-alkyl or cycloalkyl.

The compounds of formulas I and II wherein the side-chain O—Y—N=Z is attached to the meta or para position of the group Ar' are prepared according to the following flow sheet:

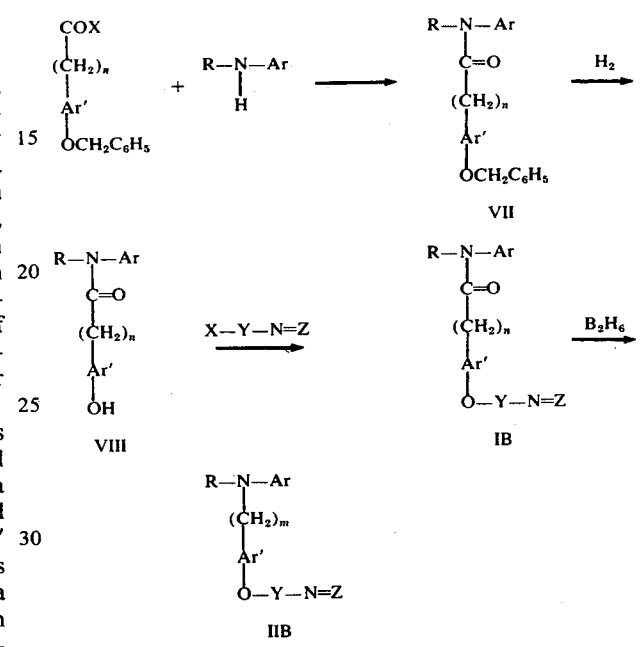

A secondary-amine of formula RNHAr is acylated with a benzyloxyaroyl halide or benzyloxyaralkanoyl halide to give an amide of formula VII. The latter is subjected to hydrogenolysis to produce the corresponding phenolic amide of formula VIII, which is then O-alkylated with an amino-lower-alkyl halide to give a compound of formula I where the side-chain —O—Y—N=Z is attached to the meta or para position of the group Ar' (IB). The amide IB can then be reduced, preferably with diborane, to give a compound of formula II where the side-chain —O—Y—N=Z is attached to the meta or para position of the group Ar' (IIB).

A further aspect of the invention resides in compounds of the formula

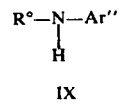

IX wherein R° is lower-alkoxyphenyl, and Ar'' is phenyl substituted in the meta or para position by the grouping —O—Y—N=Z, wherein Y is lower-alkylene and N=Z is NH₂ or a basic secondary- or tertiary-amino group having a molecular weight less than about 200, as defined for the compounds of formulas I and II. The compounds of formula IX are within the scope of formula IV of the first flow sheet above and are prepared as described above for the compounds of formula IV.

The compounds of the invention of formulas I, II and IX are basic in nature and readily form acid-addition or quaternary ammonium salts. Said acid-addition and quaternary ammonium salts are within the purview of the invention and are the full equivalents of the free bases claimed herein.

It will thus be appreciated that each of formulas I, II and IX not only represents the structural configuration of the bases of formulas I, II and IX but each is also representative of the respective structural entity which is common to all of the respective compounds of formulas I, II and IX, whether in the form of the free bases or in the form of the acid-addition or quaternary ammonium salts of the bases. By virtue of this common structural entity, the bases and their salts have inherent biological activity of a type to be more fully described hereinbelow. When used for pharmaceutical purposes one can employ the free bases themselves or the acid-addition or quaternary ammonium salts formed from pharmaceutically-acceptable acids or esters, that is, acids or esters whose anions are innocuous to the animal organism in effective doses of the salts so that beneficial properties inherent in the common structural entity represented by the free bases are not vitiated by side-effects ascribable to the anions.

In utilizing the pharmacodynamic activity of the salts of the invention, pharmaceutically-acceptable salts are preferred. Although water-insolubility, high toxicity, or lack of crystalline character may make some particular salt species unsuitable or less desirable for use as such in a given pharmaceutical application, the water-insoluble or toxic salts can be converted to any desired pharmaceutically-acceptable salt by double decomposition reactions involving the anion, for example, by ion-exchange procedures. Moreover, apart from their usefulness in pharmaceutical applications, the salts are useful as characterizing or identifying derivatives of the free bases or in isolation or purification procedures.

It will be appreciated from the foregoing that all of the acid-addition and quaternary ammonium salts of the new bases of the invention are useful and valuable compounds, regardless of considerations of solubility, toxicity, physical form, and the like, and are accordingly within the purview of the instant invention.

The novel feature of the compounds of the invention, then, resides in the concept of the bases and cationic forms of the basic compounds of formulas I, II and IX and not in any particular acid moiety or acid anion associated with the salt forms of the compounds; rather, the acid moieties or anions which can be associated in the salt forms are in themselves neither novel nor critical and therefore can be any acid anion or acid-like substance Example of salt formation with bases. In fact, in aqueous solutions, the base form or water-soluble acid-addition salt form of the compounds of the invention both possess a common protonated cation or ammonium ion.

Thus the acid-addition salts discussed above and claimed herein are prepared from any organic acid, inorganic acid (including organic acids having an inorganic group therein), or organo-metallic acid as exemplified by organic mono- and polycarboxylic acids. Illustrative acid-addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, cyclohexanesulfamic acid, mandelic acid, tropic acid, crotonic acid, acetylene dicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, isethionic acid, benzenesulfonic acid, p-toluenesulfonic acid, benzenesulfinic acid, butylarsonic acid, diethylphosphinic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

The acid-addition salts are prepared either by dissolving the free base in an aqueous solution containing the appropriate acid and isolating the salt by evaporating the solution, or by reacting the free base and acid in an organic solvent, in which case the salt separates directly or can be obtained by concentration of the solution.

The quaternary ammonium salts of the basic compounds of formulas I, II and IX are obtained by the addition of esters of strong acids to the free base form of the compounds, said esters having a molecular weight less than about 300. A preferred class of esters comprises alkyl, alkenyl, and monocarbocyclic aryl-lower-alkyl esters of strong inorganic acids or organic sulfonic acids, including such compounds as methyl chloride, methyl bromide, methyl iodide, ethyl bromide, propyl chloride, allyl chloride, allyl bromide, methyl sulfate, methyl benzenesulfonate, methyl p-toluenesulfonate, benzyl chloride, benzyl bromide, and substituted benzyl halides, for example p-chlorobenzyl chloride, 3,4-dichlorobenzyl chloride, 2,3,4,5,6-pentachlorobenzyl chloride, 4-nitrobenzyl chloride, 4-methoxybenzyl chloride, and the like.

The quaternary ammonium salts are prepared by mixing the free base and ester of a strong acid in an inert solvent. Heating may be used to facilitate the reaction, although salt formation usually takes place readily at room temperature. The quaternary ammonium salt separates directly or can be obtained by concentration of the solution.

As in the case of the acid-addition salts, water-insolubility, high toxicity, or lack of crystalline character may make some quaternary ammonium salt species unsuitable or less desirable for use as such in a given application, the water-insoluble or toxic salts can be converted to the corresponding pharmaceutically-acceptable salts by double decomposition reactions involving the anion, for example, by ion-exchange procedures. Alternatively, if the anion of the original quaternary salt forms a water-insoluble silver salt, the quaternary salt will react with silver oxide in aqueous medium to form the corresponding quaternary ammonium hydroxide, the original anion being removed as a precipitate. The quaternary ammonium hydroxide solution can then be neutralized with any desired acid, weak or strong, to produce a new quaternary ammonium salt in which the anion is different from that of the original salt. In this way quaternary ammonium salts in which the anion is derived from a weak acid are formed.

The structures of the compounds of the invention were established by the modes of synthesis, by elementary analysis, and by ultraviolet, infrared and NMR spectra.

Endocrinological evaluation of the compounds of the invention having the formulas I, II and IX by standard methods has shown that they possess hypocholesteremic activity, and are thus useful in lowering blood serum cholesterol levels in mammalian organisms. The hypocholesteremic activity was assessed by blood serum cholesterol analysis [Turner et al., Scand. J. Clin. Lab. Investigation 9, 210 (1949)] of male rats receiving the test compound by oral administration as compared with a group of control rats receiving no medication.

The actual determination of the numerical biological data definitive for a particular compound is readily obtained by standard test procedures by technicians trained in pharmacological test procedures, without the need for any extensive experimentation. They are prepared for use by conventional pharmaceutical formulation procedures used to formulate steroid hormones; that is, in capsule or tablet form with conventional excipients (for example, calcium carbonate, starch, lactose, talc, magnesium stearate, gum acacia, and the like) for oral administration; or as an aqueous or oil suspension in a pharmaceutically acceptable vehicle (aqueous alcohol, glycol, oil solution, or oil-water emulsion) for parenteral administration.

The following examples will further illustrate the invention without the latter being limited thereby.

Example 1

4-(2-Diethylaminoethoxy)diphenylamine

[IV; R is $C_6H_5$, Ar is —$C_6H_4$—(p), Y is $CH_2CH_2$, N=Z is $N(C_2H_5)_2$].

A mixture of 18.5 g. of p-anilinophenol, 7.6 g. of sodium methoxide, 35 ml. of methanol and 350 ml. of chlorobenzene was gradually heated with stirring to 130°C., while distilling off the methanol. The mixture was cooled to 75°C., and 27 g. of 2-diethylaminoethyl chloride was added. The reaction mixture was heated at reflux for 4 hours, then cooled, and 90 ml. of water and 10 ml. of 35% aqueous sodium hydroxide was added. The layers were separated, and the organic layer was dried and concentrated to remove the solvent. The residue was distilled (180°C., 10 mm.), and the 24.9 g. of product thus obtained was diluted with acetone and 28 ml. of alcoholic hydrogen chloride added. Upon cooling there separated 26.4 g. of 4-(2-diethylaminoethoxy)diphenylamine in the form of its hydrochloride salt, colorless solid, m.p. 170.5°–174.5°C., when recrystallized from isopropyl alcohol.

By replacing the p-anilinophenol in Example 1 by a molar equivalent amount of 3-anilino-6-chloro-2,4-dinitrophenol, p-(2,4-dinitroanilino)phenol, p-(2,4,5-trimethylanilino)phenol, m-(p-toluidino)phenol, p-(p-phenetidino)phenol, p-(p-bromoanilino)phenol, or p-(5-chloro-2,4-dinitroanilino)phenol, there can be obtained, respectively, 3-(2-diethylaminoethoxy)-2,6-dinitro-4-chlorodiphenylamine [IV; R is $C_6H_5$, Ar is 2,6-$(NO_2)_2$-4-Cl-$C_6H$-(m), Y is $CH_2CH_2$, N=Z is $N(C_2H_5)_2$]; 4-(2-diethylaminoethoxy)-2',4'-dinitrodiphenylamine [IV; R is 2,4-$(O_2N)_2C_6H_3$, Ar is -$C_6H_4$-(p), Y is $CH_2CH_2$, N=Z is $N(C_2H_5)_2$]; 4-(2-diethylaminoethoxy)-2',4',5'-trimethyldiphenylamine [IV; R is 2,4,5-$(CH_3)_3C_6H_2$, Ar is -$C_6H_4$-(p), Y is $CH_2CH_2$, N=Z is $N(C_2H_5)_2$]; 3-(2-diethylaminoethoxy)-4'-methyldiphenylamine [IV; R is 4-$CH_3C_6H_4$, Ar is -$C_6H_4$-(m), Y is $CH_2CH_2$, N=Z is $N(C_2H_5)_2$]; 4-(2-diethylaminoethoxy)-4'-ethoxydiphenylamine [IV; R is 4-$(C_2H_5O)C_6H_4$, Ar is -$C_6H_4$-(p), Y is $CH_2CH_2$, N=Z is $N(C_2H_5)_2$]; 4-(2-diethylaminoethoxy)-4'-bromodiphenylamine [IV; R is 4-$BrC_6H_4$, Ar is -$C_6H_4$-(p), Y is $CH_2CH_2$, N=Z is $N(C_2H_5)_2$]; or 4-(2-diethylaminoethoxy)-5'-chloro-2',4'-dinitrodiphenylamine [IV; R is 2,4-$(O_2N)_2$-5-Cl-$C_6H_2$, Ar is -$C_6H_4$-(p), Y is $CH_2CH_2$, N=Z is $N(C_2H_5)_2$].

By replacing the 2-diethylaminoethyl chloride in Example 1 by a molar equivalent amount of 2-di-(n-hexyl)aminoethyl chloride, 2-dicyclopentylaminoethyl chloride, 2-dicyclohexylaminoethyl chloride, 2-bis(4-methylcyclohexyl)aminoethyl chloride, 2-(N-cyclohexyl-N-methylamino)ethyl chloride, 2-(hexamethylenimino)ethyl chloride, 2-(4-methyl-1-piperidyl)ethyl chloride, 2-(4-morpholinyl)ethyl chloride, 2-(1-piperazinyl)ethyl chloride, 2-(4-methyl-1-piperazinyl)ethyl chloride, 2-(4-phenyl-1-piperazinyl)ethyl chloride, 2-bis(2-phenylethyl)aminoethyl chloride, 2-dibenzylaminoethyl chloride, 2-(N-benzyl-N-cyclohexylamino)ethyl chloride or 2-(N-benzyl-N-methylamino)ethyl chloride, there can be obtained, respectively, 4-[2-di-(n-hexyl)aminoethoxy]diphenylamine [IV; R is $C_6H_5$, Ar is -$C_6H_4$-(p), Y is $CH_2CH_2$, N=Z is $N(C_6H_{13})_2$]; 4-(2-dicyclopentylaminoethoxy)diphenylamine [IV; R is $C_6H_5$, Ar is -$C_6H_4$-(p), Y is $CH_2CH_2$, N=Z is $N(C_5H_9)_2$]; 4-(2-dicyclohexylaminoethoxy)diphenylamine [IV; R is $C_6H_5$, Ar is -$C_6H_4$-(p), Y is $CH_2CH_2$, N=Z is $N(C_6H_{11})_2$]; 4-[2-bis(4-methylcyclohexyl)aminoethoxy]diphenylamine [IV; R is $C_6H_5$, Ar is -$C_6H_4$-(p), Y is $CH_2CH_2$, N=Z is $N(C_6H_{10}Me)_2$]; 4-[2-(N-cyclohexyl-N-methylamino)ethoxy]diphenylamine [IV; R is $C_6H_5$, Ar is -$C_6H_4$-(p), Y is $CH_2CH_2$, N=Z is $N(C_6H_{11})(CH_3)$]; 4-[2-(hexamethylenimino)ethoxy]diphenylamine [IV; R is $C_6H_5$, Ar is -$C_6H_4$-(p), Y is $CH_2CH_2$, N=Z is $N(CH_2)_7$]; 4-[2-(4-methyl-1-piperidyl)ethoxy]diphenylamine [IV; R is $C_6H_5$, Ar is -$C_6H_4$-(p), Y is $CH_2CH_2$, N=Z is $N(CH_2)_4CHCH_3$]; 4-[2-(4-morpholinyl)ethoxy]diphenylamine [IV; R is $C_6H_5$, Ar is -$C_6H_4$-(p), Y is $CH_2CH_2$, N=Z is $N(CH_2)_4O$]; 4-[2-(1-piperazinyl)ethoxy]diphenylamine [IV; R is $C_6H_5$, Ar is -$C_6H_4$-(p), Y is $CH_2CH_2$, N=Z is $N(CH_2)_4NH$]; 4-[2-(4-methyl-1-piperazinyl)ethoxy]diphenylamine [IV; R is $C_6H_5$, Ar is -$C_6H_4$-(p), Y is $CH_2CH_2$, N=Z is $N(CH_2)_4NCH_3$]; 4-[2-(4-phenyl-1-piperazinyl)ethoxy]diphenylamine [IV; R is $C_6H_5$, Ar is -$C_6H_4$-(p), Y is $CH_2CH_2$, N=Z is $N(CH_2)_4NC_6H_5$]; 4-[2-bis(2-phenylethyl)aminoethoxy]diphenylamine [IV; R is $C_6H_5$, Ar is -$C_6H_4$-(p), Y is $CH_2CH_2$, N=Z is $N(CH_2CH_2C_6H_5)_2$]; 4-(2-dibenzylaminoethoxy)diphenylamine [IV; R is $C_6H_5$, Ar is -$C_6H_4$-(p), Y is $CH_2CH_2$, N=Z is $N(CH_2C_6H_5)_2$]; 4-[2-(N-benzyl-N-cyclohexylamino)ethoxy]diphenylamine [IV; R is $C_6H_5$, Ar is -$C_6H_4$-(p), Y is $CH_2CH_2$, N=Z is $N(C_6H_{11})(CH_2C_6H_5)$]; or 4-[2-(N-benzyl-N-benzyl-N-methylamino)ethoxy]diphenylamine [IV; R is $C_6H_5$, Ar is -$C_6H_4$-(p), Y is $CH_2CH_2$, N=Z is $N(CH_2C_6H_5)(CH_3)$]. The last three compounds named can be subjected to catalytic hydrogenolysis to give, respectively, 4-(2-aminoethoxy)diphenylamine [IV; R is $C_6H_5$, Ar is -$C_6H_4$-(p), Y is $CH_2CH_2$, N=Z is $NH_2$]; 4-(2-cyclohexylaminoethoxy)diphenylamine [IV; R is $C_6H_5$, Ar is -$C_6H_4$-(p), Y is $CH_2CH_2$, N=Z is $NH(C_6H_{11})$]; or 4-(2-methylaminoethoxy)diphenylamine [IV; R is $C_6H_5$, Ar is -$C_6H_4$-(p), Y is $CH_2CH_2$, N=Z is $NH(CH_3)$].

By replacing in Example 1 the p-anilinophenol by a molar equivalent amount of p-(p-phenetidino)phenol, and the 2-diethylaminoethyl chloride by a molar equivalent amount of 2-di-(n-hexyl)aminoethyl chloride, 2-dicyclopentylaminoethyl chloride, 2-dicyclohexylaminoethyl chloride, 2-bis(4-methylcyclohexyl)aminoethyl chloride, 2-(N-cyclohexyl-N-methylamino)ethyl chloride, 2-(hexamethylenimino)ethyl chloride, 2-(4-methyl-1-piperidyl)ethyl chloride, 2-(4-morpholinyl)ethyl chloride, 2-(1-piperazinyl)ethyl chloride, 2-(4-methyl-1-piperazinyl)ethyl chloride, 2-(4-phenyl-1-piperazinyl)ethyl chloride, 2-bis(2-phenylethyl)aminoethyl chloride, 2-dibenzylaminoethyl chloride, 2-(N-benzyl-N-cyclohexylamino)ethyl chloride or 2-(N-benzyl-N-methylamino)ethyl chloride, there can be obtained, respectively, 4-[2-di-(n-hexyl)aminoethoxy]-4'-ethoxydiphenylamine [IX; $R°$ is $4-C_2H_5OC_6H_4$, $Ar''$ is $C_6H_4OCH_2CH_2N(C_6H_{13})_2$-p]; 4-(2-dicyclopentylaminoethoxy)-4'-ethoxydiphenylamine [IX; $R°$ is $4-C_2H_5OC_6H_4$, $Ar''$ is $C_6H_4OCH_2CH_2N(C_5H_9)_2$-p]; 4-(2-dicyclohexylaminoethoxy)-4'-ethoxydiphenylamine [IX; $R°$ is $4-C_2H_5OC_6H_4$, $Ar''$ is $C_6H_4OCH_2CH_2N(C_6H_{11})_2$-p]; 4-[2-bis(4-methylcyclohexyl)aminoethoxy]-4'-ethoxydiphenylamine [IX; $R°$ is $4-C_2H_5OC_6H_4$, $Ar''$ is $C_6H_4OCH_2CH_2N(C_6H_{10}Me)_2$-p]; 4-[2-(N-cyclohexyl-N-methylamino)ethoxy]-4'-ethoxydiphenylamine [IX; $R°$ is $4-C_2H_5OC_6H_4$, $Ar''$ is $C_6H_4OCH_2CH_2N(C_6H_{11})(CH_3)$-p]; 4-[2-(hexamethylenimino)ethoxy]-4'-ethoxydiphenylamine [IX; $R°$ is $4-C_2H_5OC_6H_4$, $Ar''$ is $C_6H_4OCH_2CH_2N(CH_2)_7$-p]; 4-[2-(4-methyl-1-piperidyl)ethoxy]-4'-ethoxydiphenylamine [IX; $R°$ is $4-C_2H_5OC_6H_4$, $Ar''$ is $C_6H_4OCH_2CH_2N(CH_2)_4CHCH_3$-p]; 4-[2-(4-morpholinyl)ethoxy]-4'-ethoxydiphenylamine [IX; $R°$ is $4-C_2H_5OC_6H_4$, $Ar''$ is $C_6H_4OCH_2CH_2N(CH_2)_4O$-p]; 4-[2-(1-piperazinyl)ethoxy]-4'-ethoxydiphenylamine [IX; $R°$ is $4-C_2H_5OC_6H_4$, $Ar''$ is $C_6H_4OCH_2CH_2N(CH_2)_4NH$-p]; 4-[2-(4-methyl-1-piperazinyl)ethoxy]-4'-ethoxydiphenylamine [IX; $R°$ is $4-C_2H_5OC_6H_4$, $Ar''$ is $C_6H_4OCH_2CH_2N(CH_2)_4NCH_3$-p]; 4-[2-(4-phenyl-1-piperazinyl)ethoxy]-4'-ethoxydiphenylamine [IX; $R°$ is $4-C_2H_5OC_6H_4$, $Ar''$ is $C_6H_4OCH_2CH_2N(CH_2)_4NC_6H_5$-p]; 4-[2-bis(2-phenylethyl)aminoethoxy]-4'-ethoxydiphenylamine [IX; $R°$ is $4-C_2H_5OC_6H_4$, $Ar''$ is $C_6H_4OCH_2CH_2N(CH_2CH_2C_6H_5)_2$-p]; 4-(2-dibenzylaminoethoxy)-4'-ethoxydiphenylamine [IX; $R°$ is $4-C_2H_5OC_6H_4$, $Ar''$ is $C_6H_4OCH_2CH_2N(CH_2C_6H_5)_2$-p]; 4-[2-(N-benzyl-N-cyclohexylamino)-ethoxy]-4'-ethoxydiphenylamine [IX; $R°$ is $4-C_2H_5OC_6H_4$, $Ar''$ is $C_6H_4OCH_2CH_2N(C_6H_{11})(CH_2C_6H_5)$-p]; or 4-[2-(N-benzyl-N-methylamino)ethoxy]-4'-ethoxydiphenylamine [IX; $R°$ is $4-C_2H_5OC_6H_4$, $Ar''$ is $C_6H_4OCH_2CH_2N(CH_2C_6H_5)(CH_3)$-p]. The last three compounds named can be subjected to catalytic hydrogenolysis to give, respectively, 4-(2-aminoethoxy)-4'-ethoxydiphenylamine [IX; $R°$ is $4-C_2H_5OC_6H_4$, $Ar''$ is $C_6H_4OCH_2CH_2NH_2$-p]; 4-(2-cyclohexylaminoethoxy)-4'-ethoxydiphenylamine [IX; $R°$ is $4-C_2H_5OC_6H_4$, $Ar''$ is $C_6H_4OCH_2CH_2NH(C_6H_{11})$-p]; or 4-(2-methylaminoethoxy)-4'-ethoxydiphenylamine [IX; $R°$ is $4-C_2H_5OC_6H_4$, $Ar''$ is $C_6H_4OCH_2CH_2NH(CH_3)$-p].

According to the procedure of Example 1 the following compounds were prepared from the appropriate anilinophenol or pyridylaminophenol (R-NH-Ar-OH) and aminoalkyl halide (X—Y—N=Z):

EXAMPLE 2:

4-(3-Dimethylaminopropoxy)diphenylamine

[IV; R is $C_6H_5$, AR is $-C_6H_4$-(p), Y is $CH_2CH_2CH_2$, N=Z is $N(CH_3)_2$], b.p. 170°–190°C.(0.2 mm.), m.p. 49°–52°C. (recrystallized from benzene-hexane).

EXAMPLE 3:

4-[2-(1-Pyrrolidyl)ethoxy]diphenylamine

[IV; R is $C_6H_5$, Ar is $-C_6H_4$-(p), Y is $CH_2CH_2$, N=Z is $N(CH_2)_4$], b.p. 195°–200°C.(0.2 mm.), m.p. 75.5°–78.5°C. (recrystallized from benzene-hexane).

EXAMPLE 4:

4-(2-Dimethylaminoethoxy)diphenylamine

[IV; R is $C_6H_5$, Ar is $-C_6H_4$-(p), Y is $CH_2CH_2$, N=Z is $N(CH_3)_2$], b.p. 170°–180°C.(0.2 mm.), m.p. 75.5°–78.5°C. (orange solid from benzene-hexane).

EXAMPLE 5:

3-(2-Dimethylaminoethoxy)diphenylamine

[IV; R is $C_6H_5$, Ar is $-C_6H_4$-(m), Y is $CH_2CH_2$, N=Z is $N(CH_3)_2$], b.p. 155°–165°C.(0.05 mm.), m.p. 59°–61°C. (colorless solid from benzene-hexane).

EXAMPLE 6:

4-[2-(1-Piperidyl)ethoxy]diphenylamine

[IV; R is $C_6H_5$, Ar is $-C_6H_4$-(p), Y is $CH_2CH_2$, N=Z is $N(CH_2)_5$], m.p. 58°–59°C. (recrystallized from benzene-hexane).

EXAMPLE 7:

4-[2-(1-Pyrrolidyl)ethoxy]-4'-methoxydiphenylamine

[IV; R is $4-CH_3OC_6H_4$, Ar is $-C_6H_4$-(p), Y is $CH_2CH_2$, N=Z is $N(CH_2)_4$], b.p. 206°–210°C.(0.05 mm.), hydrochloride salt form m.p. 176°–185°C. (colorless solid from acetone).

EXAMPLE 8:

3-(3-Dimethylaminopropoxy)diphenylamine

[IV; R is $C_6H_5$, Ar is $-C_6H_4$-(m), Y is $CH_2CH_2$, N=Z is $N(CH_3)_2$], b.p. 170°–175°C.(0.05 mm.), dicyclohexylsulfamate salt form, m.p. 99°–107°C. (from acetone-ether).

EXAMPLE 9:

2-[4-(2-Dimethylaminoethoxy)anilino]pyridine

[IV; R is 2-pyridyl, Ar is $-C_6H_4$-(p), Y is $CH_2CH_2$, N=Z is $N(CH_2)_2$], m.p. 69.5°–72°C. (yellow prisms from n-hexane).

Similarly, 3-[4-(2-dimethylaminoethoxy)anilino]pyridine [IV; R is 3-pyridyl, Ar is $-C_6H_4$-(p), Y is $CH_2CH_2$, N=Z is $N(CH_3)_2$], or 4-[4-(2-dimethylaminoethoxy)anilino]pyridine [IV; R is 4-pyridyl, Ar is $-C_6H_4$-(p), Y is $CH_2CH_2$, N=Z is $N(CH_3)_2$] can be prepared from 3-(4-hydroxyanilino)pyridine or 4-(4-hydroxyanilino)pyridine, respectively, and 2-dimethylaminoethyl chloride.

EXAMPLE 10:

4-(2-Dimethylaminoethoxy)-4'-nitrodiphenylamine

[IV; R is $4-O_2NC_6H_4$, Ar is $-C_6H_4$-(p), Y is $CH_2CH_2$, N=Z is $N(CH_3)_2$], free base m.p. 121°–122.5°C. (from cyclohexane); hydrochloride salt form m.p. 171°–173°C. (from acetone-ether).

EXAMPLE 11:

4-[2-(1-Piperidyl)ethoxy]-4'-methoxydiphenylamine

[IV; R is $4-CH_3OC_6H_4$, Ar is $-C_6H_4$-(p), Y is $CH_2CH_2$, N=Z is $N(CH_2)_5$], b.p. 195°–217°C.(0.5 mm.).

EXAMPLE 12

4'-(3-Dimethylaminopropoxy)-N-phenylbenzanilide [IA; R is $C_6H_5$, AR is -$C_6H_4$-(p), Y is $CH_2CH_2CH_2$, N=Z is $N(CH_3)_2$, n is O, Ar' is $C_6H_5$].

A mixture of 10.8 g. of 4-(3-dimethylaminopropoxy)-diphenylamine (Example 2), 5.5 ml. of benzoyl chloride, 5.1 g. of sodium carbonate and 100 ml. of benzene was heated at reflux for five hours. The reaction mixture was poured into water and extracted with chloroform. The chloroform extracts were washed with water, dried and concentrated to remove the solvent. The residue was dissolved in acetone and treated with excess alcoholic hydrogen chloride, and the mixture was diluted with ether. There was thus obtained 15 g. of 4'-(3-dimethylaminopropoxy)-N-phenylbenzanilide in the form of its hydrochloride salt, colorless solid, m.p. 213°–215°C., when recrystallized from ethanol.

By replacing the 4-(3-dimethylaminopropoxy)diphenylamine in Example 12 by a molar equivalent amount of 3-(2-diethylaminoethoxy)-2,6-dinitro-4-chlorodiphenylamine, 4-(2-diethylaminoethoxy)-2',4'-dinitrodiphenylamine, 4-(2-diethylaminoethoxy)-2',-4',5'-trimethoxydiphenylamine, 3-(2-diethylaminoethoxy)-4'-methyldiphenylamine, 4-(2-diethylaminoethoxy)-4'-ethoxydiphenylamine, 4-(2-diethlaminoethoxy)-4'-bromodiphenylamine, 4-(2-diethylaminoethoxy)-5'-chloro-2',4'-dinitrodiphenylamine, 4-[2-di-(n-hexyl)aminoethoxy]diphenylamine, 4-(2-dicyclopentylaminoethoxy)diphenylamine, 4-(2-dicyclohexylaminoethoxy)diphenylamine, 4-[2-bis(4-methylcyclohexyl)aminoethoxy]diphenylamine, 4-[2-(N-cyclohexyl-N-methylamino)ethoxy]diphenylamine, 4-[2-(hexamethylenimino)-ethoxy]diphenylamine, 4-[2-(4-methyl-1-piperidyl)ethoxy]diphenylamine, 4-[2-(4-morpholinyl)ethoxy]diphenylamine, 4-[2-(1-piperazinyl)ethoxy]diphenylamine, 4-[2-(4-methyl-1-piperazinyl)ethoxy]diphenylamine, 4-[2-(4-phenyl-1-piperazinyl)ethoxy]diphenylamine, 4-[2-bis(2-phenylethyl)aminoethoxy]diphenylamine, 4-(2-dibenzylaminoethoxy)diphenylamine, 4-[2-(N-benzyl-N-cyclohexylamino)ethocy]diphenylamine, or 4-[2-(N-benzyl-N-methylamino)ethoxy]diphenylamine there can be obtained, respectively, 3'-(2-diethylaminoethoxy)-2',6'-dinitro-4'-chloro-N-phenylbenzanilide [IA; R is $C_6H_5$, Ar is 2,6-$(NO_2)_2$-4-Cl-$C_6H$-(m), Y is $CH_2CH_2$, N=Z is $N(C_2H_5)_2$, n is O, Ar' is $C_6H_5$]; 4'-(2-diethylaminoethoxy)-N-(2,4-dinitrophenyl)-benzanilide [IA; R is 2,4-$(O_2N)_2C_6H_3$, Ar is -$C_6H_4$-(p), Y is $CH_2CH_2$, N=Z is $N(C_2H_5)_2$, n is O, Ar' is $C_6H_5$]; 4'-(2-diethylaminoethoxy)-N-(2,4,5-trimethylphenyl)benzanilide [IA; R is 2,4,5-$(CH_3)_3C_6H_2$, Ar is -$C_6H_4$-(p), Y is $CH_2CH_2$, N=Z is $N(C_2H_5)_2$, n is O, Ar' is $C_6H_5$]; 3'-(2-diethylaminoethoxy)-N-(4-methylphenyl)benzanilide [IA; R is 4-$CH_3C_6H_4$, Ar is -$C_6H_4$-(m), Y is $CH_2CH_2$, N=Z is $N(C_2H_5)_2$, n is O, Ar' is $C_6H_5$]; 4'-(2-diethylaminoethoxy)-N-(4-ethoxyphenyl)benzanilide [IA; R is 4-$(C_2H_5O)C_6H_4$, Ar is -$C_6H_4$-(p), Y is $CH_2CH_2$, N=Z is $N(C_2H_5)_2$, n is O, Ar' is $C_6H_5$]; 4'-(2-diethylaminoethoxy)-N-(4-bromophenyl)benzanilide [IA; R is 4-$BrC_6H_4$, Ar is -$C_6H_4$-(p), Y is $CH_2CH_2$, N=Z is $N(C_2H_5)_2$, n is O, Ar' is $C_6H_5$]; 4'-(2-diethylaminoethoxy)-N-(5-chloro-2,4-dinitrophenyl)benzanilide [IA; R is 2,4-$(O_2N)_2$-5-Cl-$C_6H_2$, Ar is -$C_6H_4$-(p), Y is $CH_2CH_2$, N=Z is $N(C_2H_5)_2$, n is O, AR' is $C_6H_5$]; 4'-[2-di-(n-hexyl)-aminoethoxy]-N-phenylbenzanilide [IA; R is $C_6H_5$, Ar is -$C_6H_4$-(p), Y is $CH_2CH_2$, N=Z is $N(C_6H_{13})_2$, n is O, Ar' is $C_6H_5$]; 4'-(2-dicyclopentylaminoethoxy)-N-phenylbenzanilide [IA; R is $C_6H_5$, Ar is -$C_6H_4$-(p), Y is $CH_2CH_2$, N=Z is $N(C_5H_9)_2$, n is O, Ar' is $C_6H_5$]; 4'-(2-dicyclohexylaminoethoxy)-N-phenylbenzanilide [IA; R is $C_6H_5$, Ar is -$C_6H_4$-(p), Y is $CH_2CH_2$, N=Z is $N(C_6H_{11})_2$, n is O, Ar' is $C_6H_5$]; 4'-[2-bis(4-methylcyclohexyl)-aminoethoxy]-N-phenylbenzanilide [IA; R is $C_6H_5$, Ar is -$C_6H_4$-(p), Y is $CH_2CH_2$, N=Z is $N(C_6H_{10}Me)_2$, n is O, Ar' is $C_6H_5$]; 4'-[2-(N-cyclohexyl-N-methylamino)ethoxy]-N-phenylbanzanilide [IA; R is $C_6H_5$, Ar is -$C_6H_4$-(p), Y is $CH_2CH_2$, N=Z is $N(C_6H_{11})(CH_3)$, n is O, Ar']is $C_6H_5$]; 4'-[2-(hexamethylenimino)-ethoxy]-N-phenylbenzanilide [IA; R is $C_6H_5$, Ar is -$C_6H_4$-(p), Y is $CH_2CH_2$, N=Z is $N(CH_2)_7$, n is O, Ar' is $C_6H_5$]; 4'-[2-(4-methyl-1-piperidyl)ethoxy]-N-phenylbenzanilide [IA; R is $C_6H_5$, Ar is -$C_6H_4$-(p), Y is $CH_2CH_2$, N=Z is $N(CH_2)_4CHCH_3$, n is O, Ar' is $C_6H_5$]; 4'-[2-(4-morpholinyl)ethoxy]-N-phenylbenzanilide [IA; R is $C_6H_5$, Ar is -$C_6H_4$-(p), Y is $CH_2CH_2$, N=Z is $N(CH_2)_4O$, n is O, Ar' is $C_6H_5$]; 4'-[2-(1-piperazinyl)ethoxy]-N-phenylbenzanilide [IA; R is $C_6H_5$, Ar is -$C_6H_4$-(p), Y is $CH_2CH_2$, N=Z is $N(CH_2)_4NH$, n is O, Ar' is $C_6H_5$]; 4'-[2-(4-methyl-1-piperazinyl)ethoxy]-N-phenylbenzanilide [IA; R is $C_6H_5$, Ar is -$C_6H_4$-(p), Y is $CH_2CH_2$, N=Z is $N(CH_2)_4NCH_3$, n is O, Ar' is $C_6H_5$]; 4'-[2-(4-phenyl-1-piperazinyl)ethoxy]-N-phenylbenzanilide [IA; R is $C_6H_5$, Ar is -$C_6H_4$-(p), Y is $CH_2CH_2$, N=Z is $N(CH_2)_4NC_6H_5$, n is O, Ar' is $C_6H_5$]; 4'-[2-bis(2-phenylethyl)aminoethoxy]-N-phenylbenzanilide [IA; R is $C_6H_5$, Ar is -$C_6H_4$-(p), Y is $CH_2CH_2$, N=Z is $N(CH_2CH_2C_6H_5)_2$, n is O, Ar' is $C_6H_5$]; 4'-(2-dibenzylaminoethoxy)-N-phenylbenzanilide [IA; R is $C_6H_5$, Ar is -$C_6H_4$-(p), Y is $CH_2CH_2$, N=Z is $N(CH_2C_6H_5)_2$, n is O, Ar' is $C_6H_5$]; 4'-[2-(N-benzyl-N-cyclohexylamino)ethoxy]-N-phenylbenzanilide [IA; R is $C_6H_5$, Ar is -$C_6H_4$-(p), Y is $CH_2CH_2$, N=Z is $N(C_6H_{11})(CH_2C_6H_5)$, n is O, Ar' is $C_6H_5$]; or 4'-[2-(N-benzyl-N-methylamino)ethoxy]-N-phenylbenzanilide ]IA; R is $C_6H_5$, Ar is -$C_6H_4$-(p), Y is $CH_2CH_2$, N=Z is $N(CH_2C_6H_5)(CH_3)$, n is O, Ar' is $C_6H_5$]. The last three compounds named can be subjected to catalytic hydrogenolysis to give, respectively, 4'-(2-aminoethoxy)-N-phenylbenzanilide [IA; R is $C_6H_5$, Ar is -$C_6H_4$-(p), Y is $CH_2CH_2$, N=Z is $NH_2$, N is O, Ar' is $C_6H_5$]; 4'-(2-cyclohexylaminoethoxy)-N-phenylbenzanilide [IA; R is $C_6H_5$, Ar is -$C_6H_4$-(p), Y is $CH_2CH_2$, N=Z is $NH(C_6H_{11})$, n is O, Ar' is $C_6H_5$]; or 4'-(2-methylaminoethoxy)-N-phenylbenzanilide [IA; R is $C_6H_5$, Ar is -$C_6H_4$-(p), Y is $CH_2CH_2$, N=Z is $NH(CH_3)$, n is O, Ar' is $C_6H_5$].

According to the procedure of Example 12 the following compounds were prepared from the appropriate diphenylamine of formula IV and aroyl or aralkanoyl halide, Ar'-$(CH_2)_n$COX:

EXAMPLE 13:

4'-(3-Dimethylaminopropoxy)-2-methoxy-N-phenylbenzanilide [IA; R is $C_6H_5$, Ar is -$C_6H_4$-(p), Y is $CH_2CH_2CH_2$, N=Z is $N(CH_3)_2$, n is O, Ar' is $C_6H_4OCH_3$-2], dicyclohexanesulfamate salt form, colorless solid, m.p. 112°–117°C. (from acetone-ether).

EXAMPLE 14:

4'-[2-(1-Pyrrolidyl)ethoxy]-N-phenylbenzanilide [IA; R is $C_6H_5$, Ar is -$C_6H_4$-(p), Y is $CH_2CH_2$, N=Z is $N(CH_2)_4$, n is O, Ar' is $C_6H_5$], colorless solid, m.p. 85.5°–87.5°C. (from benzene-hexane).

EXAMPLE 15:

4'-(2-Dimethylaminoethoxy)-4-chloro-N-phenylbenzanilide

[IA; R is $C_6H_5$, Ar is -$C_6H_4$-(p), Y is $CH_2CH_2$, N=Z is $N(CH_3)_2$, n is O, Ar' is $C_6H_4Cl$-4], colorless solid, m.p. 101°–104°C. (from benzene-pentane).

EXAMPLE 16:

4'-(2-Dimethylaminoethoxy)-4-methoxy-N-phenylbenzanilide

[IA; R is $C_6H_5$, Ar is -$C_6H_4$-(p), Y is $CH_2CH_2$, N=Z is $N(CH_3)_2$, n is O, Ar' is $C_6H_4OCH_3$-4], free base form, m.p. 94°–111°C. (from benzene-hexane); hydrochloride salt form, colorless solid, m.p. 165°–169°C. (from isopropyl alcohol-ether).

EXAMPLE 17:

4'-(3-Dimethylaminopropoxy)-4-methyl-N-phenylbenzanilide

[IA; R is $C_6H_5$, Ar is -$C_6H_4$-(p), Y is $CH_2CH_2CH_2$, N=Z is $N(CH_3)_2$, n is O, Ar' is $C_6H_4CH_3$-4], hydrochloride salt form, colorless solid, m.p. 161°–165°C. (from isopropyl alcohol-ether).

EXAMPLE 18:

4'-(2-Dimethylaminoethoxy)-4-methyl-N-phenylbenzanilide

[IA; R is $C_6H_5$, Ar is -$C_6H_4$-(p), Y is $CH_2CH_2$, N=Z is $N(CH_3)_2$, n is O, Ar' is $C_6H_4CH_3$-4], colorless solid, m.p. 74.5°–77.5°C. (from benzene-hexane).

EXAMPLE 19:

4'-(2-Dimethylaminoethoxy)-4-fluoro-N-phenylbenzanilide

[IA; R is $C_6H_5$, Ar is -$C_6H_4$-(p), Y is $CH_2CH_2$, N=Z is $N(CH_3)_2$, n is O, Ar' is $C_6H_4F$-4], colorless solid, m.p. 88.5°–90°C. (from benzene-pentane).

EXAMPLE 20:

4'-(2-Diethylaminoethoxy)-4-nitro-N-phenylbenzanilide

[IA; R is $C_6H_5$, Ar is -$C_6H_4$-(p), Y is $CH_2CH_2$, N=Z is $N(C_2H_5)_2$, n is O, Ar' is $C_6H_4NO_2$-4], hydrochloride salt form, tan solid, m.p. 190°–192°C. (from ethanol-ether).

EXAMPLE 21:

4'-(3-Dimethylaminopropoxy)-2-methyl-N-phenylbenzanilide

[IA; R is $C_6H_5$, Ar is -$C_6H_4$-(p), Y is $CH_2CH_2CH_2$, N=Z is $N(CH_3)_2$, n is O, Ar' is $C_6H_4CH_3$-2], dicyclohexanesulfamate salt form, colorless solid, m.p. 116°–121°C. (from acetone-ether).

EXAMPLE 22:

4'-(2-Dimethylaminoethoxy)-2-methyl-N-phenylbenzanilide

[IA; R is $C_6H_5$, Ar is -$C_6H_4$-(p), Y is $CH_2CH_2$, N=Z is $N(CH_3)_2$, n is O, Ar' is $C_6H_4CH_3$-2], colorless solid, m.p. 98.5°–102.5°C. (from benzene-hexane).

EXAMPLE 23:

4'-(3-Dimethylaminopropoxy)-4-nitro-N-phenylbenzanilide

IA; R is $C_6H_5$, Ar is -$C_6H_4$-(p), Y is $CH_2CH_2CH_2$, N=Z is $N(CH_3)_2$, n is O, Ar' is $C_6H_4NO_2$-4], yellow solid, m.p. 89.5°–92.5°C. (from benzene-hexane).

EXAMPLE 24:

4'-(3-Dimethylaminopropoxy)-3-methyl-N-phenylbenzanilide

[IA; R is $C_6H_5$, Ar is -$C_6H_4$-(p), Y is $CH_2CH_2CH_2$, N=Z is $N(CH_3)_2$, n is O, Ar' is $C_6H_4CH_3$-3], cyclohexanesulfamate salt form, colorless solid, m.p. 163°–165°C. (from ethanol).

EXAMPLE 25:

4'-(3-Dimethylaminopropoxy)-4-fluoro-N-phenylbenzanilide

[IA; R is $C_6H_5$, Ar is -$C_6H_4$-(p), Y is $CH_2CH_2CH_2$, N=Z is $N(CH_3)_2$, n is O, Ar' is $C_6H_4F$-4], colorless solid, m.p. 82.5°–83.5°C. (from benzene-hexane).

EXAMPLE 26:

4'-[2-(1-Pyrrolidyl)ethoxy]-4-methoxy-N-phenylbenzanilide

[IA; R is $C_6H_5$, Ar is -$C_6H_4$-(p), Y is $CH_2CH_2$, N=Z is $N(CH_2)_4$, n is O, Ar' is $C_6H_4OCH_3$-4], light tan solid, m.p. 112°–115°C. (from benzene-hexane).

EXAMPLE 27:

4'-(2-Dimethylaminoethoxy)-N-phenylbenzanilide

[IA; R is $C_6H_5$, Ar is -$C_6H_4$-(p), Y is $CH_2CH_2$, N=Z is $N(CH_3)_2$, n is O, Ar' is $C_6H_5$], hydrochloride salt form, colorless solid, m.p. 175°–179°C. (from ethanol-ether).

EXAMPLE 28:

4'-[2-(1-Piperidyl)ethoxy]-4-methoxy-N-phenylbenzanilide

[IA; R is $C_6H_5$, Ar is -$C_6H_4$-(p), Y is $CH_2CH_2$, N=Z is $N(CH_2)_5$, n is O, Ar' is $C_6H_4OCH_3$-4], hydrochloride salt form, colorless solid, m.p. 181.5°–185.5°C. (from ethanol-ether).

EXAMPLE 29:

4'-[2-(1-Piperidyl)ethoxy]-4-methyl-N-phenylbenzanilide

[IA; R is $C_6H_5$, Ar is -$C_6H_4$-(p), Y is $CH_2CH_2$, N=Z is $N(CH_2)_5$, n is O, Ar' is $C_6H_4CH_3$-4], colorless solid, m.p. 72.5°–75.5°C. (from benzene-hexane and from hexane).

EXAMPLE 30:

4'-(2-Dimethylaminoethoxy)-2-methoxy-N-phenylbenzanilide

[IA; R is $C_6H_5$, Ar is -$C_6H_4$-(p), Y is $CH_2CH_2$, N=Z is $N(CH_3)_2$, n is O, Ar' is $C_6H_4OCH_3$-2], colorless solid, m.p. 82.5°–85.5°C. (from benzene-hexane).

EXAMPLE 31:

4'-(3-Dimethylaminopropoxy)-2,4-dimethoxy-N-phenylbenzanilide

[IA; R is $C_6H_5$, Ar is -$C_6H_4$-(p), Y is $CH_2CH_2CH_2$, N=Z is $N(CH_3)_2$, n is O, Ar' is $C_6H_3(OCH_3)_2$-2,4], colorless solid, m.p. 78.5°–82.5°C. (from benzene-hexane).

EXAMPLE 32:

4'-(3-Dimethylaminopropoxy)-3-methoxy-N-phenylbenzanilide

[IA; R is $C_6H_5$, Ar is -$C_6H_4$-(p), Y is $CH_2CH_2CH_2$, N=Z is $N(CH_3)_2$, n is O, Ar' is $C_6H_4OCH_3$-3], cyclohexanesulfamate salt form, colorless solid, m.p. 173°–176°C. (from acetone).

EXAMPLE 33:

4'-(3-Dimethylaminopropoxy)-2,N-diphenylacetanilide

[IA; R is $C_6H_5$, Ar is $-C_6H_4$-(p), Y is $CH_2CH_2CH_2$, N=Z is $N(CH_3)_2$, n is 1, Ar' is $C_6H_5$], dicyclohexanesulfamate salt form, pale green solid, m.p. 82.5°–86.5°C. (from acetone-ether).

Similarly, 4-(3-dimethylaminopropoxy)diphenylamine and gamma-phenylbutyryl chloride react to form 4'-(3-dimethylaminopropoxy)-4, N-diphenylbutyranilide [IA; R is $C_6H_5$, Ar is $-C_6H_4$-(p), Y is $CH_2CH_2CH_2$, N=Z is $N(CH_3)_2$, n is 3, Ar' is $C_6H_5$].

EXAMPLE 34:

3'-(2-Dimethylaminoethoxy)-N-phenylbenzanilide

[IA; R is $C_6H_5$, Ar is $-C_6H_4$-(m), Y is $CH_2CH_2$, N=Z is $N(CH_3)_2$, n is O, Ar' is $C_6H_5$], dicyclohexanesulfamate salt form, colorless solid, m.p. 110°–112°C. (from ethanol-ether).

EXAMPLE 35:

4'-(2-Dimethylaminoethoxy)-4-nitro-N-phenylbenzanilide

[IA; R is $C_6H_5$, Ar is $-C_6H_4$-(p), Y is $CH_2CH_2$, N=Z is $N(CH_3)_2$, n is O, Ar' is $C_6H_4NO_2$-4], m.p. 98°–101°C. (from ethyl acetate-hexane).

EXAMPLE 36:

4'-[2-(1-Pyrrolidyl)ethoxy]-N-(4-methoxyphenyl)benzanilide

[IA; R is $4-Ch_3OC_6H_4$, Ar is $-C_6H_4$-(p), Y is $CH_2CH_2$, N=Z is $N(CH_2)_4$, n is O, Ar' is $C_6H_5$], colorless solid, m.p. 104°–110°C. (from isopropyl alcohol and from ether).

EXAMPLE 37:

3'-(3-Dimethylaminopropoxy)-N-phenylbenzanilide

[IA; R is $C_6H_5$, Ar is $-C_6H_4$-(m), Y is $CH_2CH_2CH_2$, N=Z is $N(CH_3)_2$, n is O, Ar' is $C_6H_5$], p-toluenesulfonate salt form, colorless solid, m.p. 77°–81°C. (from ethyl acetate).

EXAMPLE 38:

4'-(2-Dimethylaminoethoxy)-2,N-diphenylacetanilide

[IA; R is $C_6H_5$, Ar is $-C_6H_4$-(p), Y is $CH_2CH_2$, N=Z is $N(CH_3)_2$, n is 1, Ar' is $C_6H_5$].

EXAMPLE 39:

4'-(2-Dimethylaminoethoxy)-N-(2-pyridyl)benzanilide

[IA; R is 2-pyridyl, Ar is $-C_6H_4$-(p), Y is $CH_2CH_2$, N=Z is $N(CH_3)_2$, n is O, Ar' is $C_6H_5$], tan solid, m.p. 76.5°–78.8°C. (from cyclohexane).

Similarly, 4'-(2-dimethylaminoethoxy-N-(3-pyridyl)benzanilide [IA; R is 3pyridyl, Ar is $-C_6H_4$-(p), Y is $CH_2CH_2$, N=Z is $N(CH_3)_2$, n is O, Ar' is $C_6H_5$]or 4'-(2-dimethlaminoethoxy)-N-(4-pyridyl)benzanilide [IA; R is 4-pyridyl, Ar is $-C_6H_4$-(p), Y is $CH_2CH_2$, N=Z is $N)CH_3)_2$, n is O, Ar' is $C_6H_5$] can be prepared by reacting 3-[4-(2-dimethylaminoethoxy)anilino]-pyridine or 4-[4-(2-dimethylaminoethoxy)anilino]pyridine, respectively, with benzoyl chloride.

EXAMPLE 40

4'-[2-(1-Piperidyl)ethoxy]-N-(4-methoxyphenyl)benzanilide

[IA; R is $4-CH_3OC_6H_4$, Ar is $-C_6H_4$-(p), Y is $CH_2CH_2$, N=Z is $N(CH_2)_5$, n is O, Ar' is $C_6H_5$], tan solid, m.p. 107.5°–108.5°C. (from ether).

EXAMPLE 41:

4'-(2-Dimethylaminoethoxy)-N-(4-methoxyphenyl)benzanilide

[IA; R is $4-CH_3OC_6H_4$, Ar is $-C_6H_4$-(p), Y is $CH_2CH_2$, N=Z is $N(CH_3(_2$, n is O, Ar' is $C_6H_5$], colorless prisms, m.p. 90°–91.5°C. (from ether).

EXAMPLE 42

4-(2-Dimethylaminoethoxy)-N-(4-chlorobenzyl)diphenylamine

[IIA; R is $C_6H_5$, Ar is $-C_6H_4$-(p), Y is $CH_2CH_2$, N=Z is $N)CH_3)_2$, m is 1, Ar' is $C_6H_4Cl$-4].

A solution of 19.0 g. of 4'-(2-dimethylaminoethoxy)-4-chloro-N-phenylbenzanilide (Example 15) in 400 ml. of tetrahydrofuran was slowly added with stirring to 77 ml. of a one molar solution of diborane in tetranydrofuran held in an ice-salt bath under anhydrous conditions. The reaction mixture was then warmed and heated at reflux for 2½ hours. The mixture was cooled and 150 ml. of water containing 16 ml. of 6N hydrochloric acid was slowly added. The tetrahydrofuran was distilled off and the remaining aqueous mixture saturated with sodium hydroxide. The mixture was then extracted with ether and the ether extracts dried and concentrated. The residue was dissolved in acetone and treated with excess alcoholic hydrogen chloride. The solution was diluted with ether which caused separation of 4-(2-dimethylaminoethoxy)-N-(4-chlorobenzyl)-diphenylamine in the form of its hydrochloride salt, aqua colored solid, m.p. 140.5°–145.5°C. when recrystallized from isopropyl alcohol.

By replacing the 4'-(2-dimethylaminoethoxy)-4-chloro-N-phenylbenzanilide in Example 42 by a molar equivalent amount of 3'-(2-diethylaminoethoxy-2',6'-dinitro-4'-chloro-N-phenyl benzanilide, 4'-(2-diethylaminoethoxy)-N-(2,4-dinitrophenyl)benzanilide, 4'-(2-diethylaminoethoxy)-N-(2,4,5-trimethylphenyl)benzanilide, 3'-(2-diethylaminoethoxy)-N-(4-methylphenyl)benzanilide, 4'-(2-diethylaminoethoxy)-N-(4-ethoxyphenyl)benzalide, 4'-(2-diethylaminoethoxy)-N-(4-bromophenyl)benzanilide, 4'-(2-diethylaminoethoxy)-N-(5-chloro-2,4-dinitrophenyl)benzanilide, 4'-[b 2-di-(n-hexyl)aminoethoxy]-N-phenylbenzanilide, 4'-(2-dicyclopentylaminoethoxy-N-phenylbenzanilide, 4'-(2-dicyclohexylaminoethoxy)-N-phenylbenzanilide, 4'-[2-bis(4-methylcyclohexyl)aminoethoxy]-N-phenylbenzanilide, 4'-[2-(N-cyclohexyl-N-methylamino)ethoxy]N-phenylbenzanilide, 4'-[2-(hexamethylenimino)ethoxy]-N-phenylbenzanilide, 4'-[2(4-methyl-1-piperidyl)ethoxy]-N-phenylbenzanilide, 4'-[2-(4-morpholinyl)ethoxy]-N-phenylbenzanilide, 4'-[2-(1piperazinyl)ethoxy]-N-phenylbenzanilide, 4'-[2-(4-methyl-1-piperazinyl)ethoxy]-N-phenylbenzanilide, 4'-[2-(4-phenyl-1-piperazinyl)ethoxy]-N-phenylbenzanilide, 4'-[2-bis(2-phenylethyl)aminoethoxy]-N-phenylbenzanilide, 4'-(2-dibenzylaminoethoxy)-N-phenylbenzanilide, 4'-[2-(N-benzyl-N-cyclohexylamino)ethoxy]-N-phenhybenzanilide, or 4'-[2-(N-benzyl-N-methylamino)ethoxy]-N-phenylbenzanilide there can be obtained, respectively, 3-(2-diethylaminoethoxy)-2,6--dinitro-4-chloro-N-benzyldephenylamine [IIA; R is $C_6H_5$, Ar is $2,6-(NO_2)_2-4-Cl-C_6H_4$-(m), Y is $CH_2CH_2$, N=Z is $N(C_2H_5)_2$, m is 1, Ar'is $C_6H_5$]; 4-(2-diethylaminoethoxy)-2',4'-dinitro-N-benzyldiphenylamine [IIA; R is 2,4-$(O_2N)_2C_6H_3$, Ar is -$C_6H_4$-(p), Y is $CH_2CH_2$, N=Z is $N(C_2H_5)_2$, $m$ is 1, Ar' is $C_6H_5$]; 4-(2-diethylaminoethoxy)-2',4',5'-trimethyl-N-benzyldiphenylamine [IIA; R is 2,4,5-$(CH_3)_3C_6H_2$, Ar is -$C_6H_4$-(p), Y is $CH_2CH_2$, N=Z is $N(C_2H_5)_2$, $m$ is 1, Ar' is $C_6H_5$]; 3-(2-diethylaminoethoxy)-4'-methyl-N-benzyldiphenylamine [IIA; R is 4-$CH_3C_6H_4$, Ar is -$C_6H_4$-($m$), Y is $CH_2CH_2$, N=Z is $N(C_2H_5)_2$, $m$ is 1, Ar'is $C_6H_5$]; 4-(2-diethylaminoethoxy)-4'-ethoxy-N-benzyldiphenylamine [IIA; R is 4-$(C_2H_5O)C_6H_4$, Ar is -$C_6H_4$-(p), Y is $CH_2CH_2$, N=Z is $N(C_2H_5)_2$, $m$ is 1, Ar'is $C_6H_5$]; 4-(2-diethylaminoethoxy)-4'-bromo-N-benzyldiphenylamine [IIA; R is 4-$BrC_6H_4$, Ar is -$C_6H_4$-(p), Y is $CH_2CH_2$, N=Z is $N(C_2H_5)_2$, $m$ is 1, Ar'is $C_6H_5$]; 4-(2-diethylaminoethoxy)-5'-chloro-2',4'-dinitro-N-benzyldiphenylamine [IIA; R is 2,4-$(O_2N)_2$-5-Cl-$C_6H_2$, Ar is -$C_6H_4$-(p), Y is $CH_2CH_2$, N=Z is $N(C_2H_5)_2$, $m$ is 1, Ar' is $C_6H_5$]; 4-[2-di-(n-hexyl)aminoethoxy]-N-benzyldiphenylamine [IIA; R is $C_6H_5$, Ar is -$C_6H_4$-(p), Y is $CH_2CH_2$, N=Z is $N(C_6H_{13})_2$, $m$ is 1, Ar' is $C_6H_5$]; 4-(2-dicyclopentylaminoethoxy)-N-benzyldiphenylamine [IIA; R is $C_6H_5$, Ar is -$C_6H_4$-(p), Y is $CH_2CH_2$, N=Z is $N(C_5H_9)_2$, $m$ is 1, Ar' is $C_6H_5$]; 4'-(2-dicyclohexylaminoethoxy)-N-benzyldiphenylamine [IIA; R is $c_6H_5$, Ar is -$C_6H_4$-(p), Y is $CH_2CH_2$, N=Z is $N(C_6H_{11})_2$, $m$ is 1, Ar' is $C_6H_5$]; 4'-[2-bis(4-methylcyclohexyl)aminoethoxyl]-N-benzyldiphenylamine [IIA; R is $C_6H_5$, Ar is -$C_6H_4$-(p), Y is $CH_2CH_2$, N=Z is $N(C_6H_{10}Me)_2$, $m$ is 1, Ar' is $C_6H_5$]; 4-[2-(n-cyclohexyl-N-methylamino)ethoxy]-N-benzyldiphenylamine [IIA; R is $C_6H_5$, Ar is -$C_6H_4$-(p), Y is $CH_2CH_2$, N=Z is $N(C_6H_{11})(CH_3)$, $m$ is 1, Ar' is $C_6H_5$ ; 4[2-(hexamethyenimino)-ethoxy]-N-benzyldiphenylamine [IIA; R is $C_6H_5$, Ar is -$C_6H_4$-(p), Y is $CH_2CH_2$, N=Z is $N(CH_2)_7$, $m$ is 1, Ar' is $C_6H_5$]; 4-[2-(4-methyl-1-piperidyl)ethoxy]-N-benzyldiphenylamine [IIA; R is $C_6H_5$, Ar is -$C_6H_4$-(p), Y is $CH_2CH_2$, N=Z is $N(CH_2)_4CHCH_3$, $m$ is 1, Ar' is $C_6H_5$]; 4-[2-(4-morpholinyl)ethoxy]-N-benzyldiphenylamine [IIA; R is $C_6H_5$, Ar is -$C_6H_4$-(p), Y is $CH_2CH_2$, N=Z is $N(CH_2)_4O$, $m$ is 1, Ar' is $C_6H_5$]; 4-[2-(1-piperazinyl)ethoxy]-N-benzyldiphenylamine [IIA; R is $C_6H_5$, Ar is -$C_6H_4$-(p), Y is $CH_2CH_2$, N=Z is $N(CH_2)_4NH$, $m$ is 1, Ar' is $C_6H_5$]; 4-[2l -(4-methyl-1-piperazinyl)ethoxy]-N-benzyldiphenylamine [IIA; R is $C_6H_5$, Ar is -$C_6H_4$(p), Y is $CH_2CH_2$, N=Z is $N(CH_2)_4NCH_3$, $m$ is 1, Ar'is $C_6H_5$]; 4-[2-(4-phenyl1-piperazinyl)ethoxy]-N-benzyldiphenylamine [IIA; R is $C_6H_5$, Ar is -$C_6H_4$-(p), Y is $CH_2CH_2$, N=Z is $N(CH_2(_4NC_6H_5$, $m$ is 1, Ar'is $C_6H_5$] ; 4-[2-bis(2-phenylethyl)aminoethoxy]-N-benzylidiphenylamine [IIA; R is $C_6H_5$, Ar is -$C_6H_4$-(p), Y is $CH_2CH_2$, N=Z is $N(CH_2CH_2C_6H_5)_2$, $m$ is 1, Ar' is $C_6H_5$]; 4-(2-dibenzylaminoethoxy)-N-benzyldiphenylamine [IIA; R is $C_6H_5$, Ar is -$C_6H_4$-(p), Y is $CH_2CH_2$, N=Z is $N(CH_2C_6H_5)_2$, $m$ is 1, Ar' is $C_6H_5$]; 4-[2-(N-benzyl-N-cyclohexylamino)ethoxy]-N-benzyldiphenylamine [IIA; R is $C_6H_5$, Ar is -$C_6H_4$-(p), Y is $CH_2CH_2$, N=Z is $N(C_6H_{11})(CH_2C_6H_5)$, $m$ is 1, Ar' is $C_6H_5$]; or 4-[2-(N-benzyl-N-methylamino)ethoxy]-N-benzyldiphenylamine [IIA; R is $C_6H_5$, Ar is -$C_6H_4$-(p), Y is $CH_2CH_2$, N=Z is $N(CH_2C_6H_5)(CH_3)$, $m$ is 1, Ar' is $C_6H_5$]. The last three compounds named can be subjected to catalytic hydrogenolysis to give, respectively, 4-(2-aminoethoxy)-N-benzyldiphenylamine [IIA; R is $C_6H_5$, Ar is -$C_6H_4$-(p), Y is $CH_2CH_2$, N=Z is $NH_2$, $m$ is 1, Ar' is $C_6H_5$] ; 4-(2-cyclohexylaminoethoxy)-N-benzyldiphenylamine [IIA; R is $C_6H_5$, Ar is -$C_6H_4$-(p), Y is $CH_2CH_2$, N=Z is $NH(C_6H_{11})$, $m$ is 1, Ar' is $C_6H_5$]; or 4-(2-methylaminoethoxy)-N-benzyldiphenylamine [IIA; R is $C_6H_5$, Ar is -$C_6H_4$-(p), Y is $CH_2CH_2$N=Z is $NH(CH_3)$, 2, is 1, Ar' is $C_6H_5$].

Similarly, 4'-(2-dimethylaminoethoxy)-N-(3-pyridyl)-benzanilide, 4'-(2-dimethylaminoethoxy)-N-(4-pyridyl)benzanilide or 4'-(3-dimethylaminopropoxy)-4, N-diphenylbutyranilide can be reduced with diborane to give N-[4'-(2-dimethylaminoethoxy)]-N-(3-pyridyl)benzylamine [IIA; R is 3-pyridyl, Ar is -$C_6H_4$-(p), Y is $CH_2CH_2$, N=Z is $N(CH_3)_2$, $m$ is 1, Ar' is $C_6H_5$]; N-[4'-(2-dimethylaminoethoxy)]-N-(4-pyridyl)benzylamine [IIA; R is 4-pyridyl, Ar is -$C_6H_4$-(p), Y is $CH_2CH_2$, N=Z is $N(CH_3)_2$, $m$ is 1, Ar' is $C_6H_5$]; or 4-(3-dimethylaminopropoxy)-N-(4-phenylbutyl)diphenylamine [IIA; R is $C_6H_5$, Ar is -$C_6H_4$-(p), Y is $CH_2CH_2CH_2$, N=Z is $N(CH_3)_2$, $m$ is 4, Ar' is $C_6H_5$].

According to the procedure of Example 42 the following compounds were prepared by diborane reduction of the appropriate benzanilide derivative of formula IA:

EXAMPLE 43:

4-(3-Dimethylaminopropyl)-N-(2-methoxybenzyl)-diphenylamine

[IIA; R is $C_6H_5$, Ar is -$C_6H_4$-(p), Y is $CH_2CH_2CH_2$, N=Z is $N(CH_3)_2$, $m$ is 1, Ar' is $C_7H_4OCH_3$-2], dicyclohexanesulfamate salt form, pale yellow solid, m.p. 106°–111°C. (from acetone-ether).

EXAMPLE 44:

4-(2-Dimethylaminoethoxy)-N-(4-nitrobenzyl)diphenylamine

[IIA; R is $C_6H_5$, Ar is -$C_6H_4$-(p), Y is $CH_2CH_2$, N=Z is $N(CH_3)_2$, $m$ is 1, Ar' is $C_6H_4NO_2$-4], cyclohexanesulfamate salt form, yellow solid, m.p. 152.5°–158.5°C. (from ethanol).

EXAMPLE 45:

3-(2-Dimethylaminoethoxy)-N-benzyldiphenylamine

[IIA; R is $C_6H_5$, Ar is -$C_6H_4$-(p), Y is $CH_2CH_2$, N=Z is $N(CH_3)_2$, $m$ is 1, Ar ' is $C_6H_5$], hydrochloride salt form, colorless solid, m.p. 165°–170°C. (from acetone-ether).

EXAMPLE 46:

4-(2-Dimethylaminoethoxy)-N-(2-phenylethyl)diphenylamine

[IIA; R is $C_6H_5$, Ar is -$C_6H_4$-(p), Y is $CH_2CH_2$, N=Z is $N(CH_3)_2$, $m$ is 2, Ar' is $C_6H_5$], free base form. b.p. 158°–164°C.(0.05 mm.), m.p. 68°–72°C. (from hexane); hydrochloride salt form, colorless solid, m.p. 172°–175°C. (from isopropyl alcohol).

EXAMPLE 47:

4-[2-(1-Pyrrolidyl)ethoxy]-4'-methoxy-N-benzyldiphenylamine

[IIA; R is 4-$CH_3OC_6H_4$, Ar is -$C_6H_4$-(p), Y is $CH_2CH_2$, N=Z is $N(CH_2)_4$, $m$ is 1, Ar' is $C_6H_5$], cyclohexanesulfamate salt form, colorless solid, m.p. 128°–132.5°C. (from acetone-ether).

EXAMPLE 48:

4-(2-Dimethylaminoethoxy)-N-(2-methoxybenzyl)-diphenylamine

[IIA; R is $C_6H_5$, Ar is -$C_6H_4$-(p), Y is $CH_2CH_2$, $N=Z$ is $N(CH_3)_2$, $m$ is 1, Ar' is $C_6H_4OCH_3$-2], free base form, colorless crystals, m.p. 81°–83°C. (from ether); hydrochloride salt form, m.p. 136°–141°C. (from acetone-ether).

EXAMPLE 49:

4-[2-(1-Piperidyl)ethoxy ]-4-methoxy-N-benzyldiphenylamine

[IIA; R is 4-$CH_3OC_6H_4$, Ar is -$C_6H_4$-(p), Y is $CH_2CH_2$, N=Z is $N(CH_2)_5$, m is 1, Ar' is $C_6H_5$], cyclohexanesulfamate salt form, light tan prisms, m.p. 138°–139°C. (from isopropyl alcohol-ether).

EXAMPLE 50:

4-(2-Dimethylaminoethoxy))-4-methoxy-N-benzyldiphenylamine

[IIA; R is 4-$CH_3OC_6H_4$, Ar is -$C_6H_4$-(p), Y is $CH_2CH_2$, N=Z is $N(CH_3)_2$, m is 1, Ar' is $C_6H_5$].

EXAMPLE 51 a. 4'-Benzyloxy-4phenylbenzanilide [V; R is $C_6H_5$, Ar is -$C_6H_4$-(p), R' is $CH_2C_6H_5$, n is O, Ar' is $C_6H_4OCH_3$-4] was prepared from 41.3 g. of 4-benzyloxydiphenylamine and 30.8 g. of p-anisoyl chloride according to the procedure of Example 12. There was thus obtained 37.8 g. of 4'-benzyloxy-4-methoxy-N-phenylbenzanilide, m.p. 134.5°–136.5°C.

b. 4'-Hydroxy-4-methoxy-N-phenylbenzanilide [V; R is $C_6H_5$, Ar is -$C_6H_4$-(p), R' is H, n is O, Ar' is $C_6H_4OCH_3$-4].

4'-Benzyloxy-4-methoxy-N-phenylbenzanilide (8.2 g.) in 200 ml. of acetic acid was hydrogenated in the presence of 3 of 10% palladium-on-carbon catalyst. After hydrogenolysis was completed, the catalyst was filtered off and the filtrate evaporated to remove the solvent. The residue was dissolved in ethanol and water added to the point of turbidity. The solid product which separated was collected and recrystallized from aqueous ethanol to give 4'-hydroxy-4-phenylbenzamilide, m.p. 195°–199°C.

c. 4'-(3-Dimethylaminopropoxy)-4-methoxy-N-phenylbenzanilide [IA; R is $C_6H_5$, Ar is -$C_6H_4$-(p), Y is $CH_2CH_2CH_2$, N=Z is $N(CH_3)_2$, n is O, Ar' is $C_6H_4OCH_3$-4] was prepared from 5.5 g. of 4'-hydroxy-4-methoxy-N-phenylbenzanilide and 4.2 g. of 2-dimethylaminoethyl chloride in the presence of sodium methoxide according to the procedure of Example 1. The product was recrystallized from benzene-hexane to give 4'-(3-dimethylaminopropoxy)-4-methoxy-N-phenylbenzanilide, colorless solid, m.p. 111°–115°C.

EXAMPLE 52 a. 4'-Benzyloxy-4-chloro-N-phenylbenzanilide [V; R is $C_6H_5$, Ar is -$C_6H_4$-(p), R' is $CH_2C_6H_5$, n is O, Ar' is $C_6H_4$cl-4] was prepared from 137.5 g. of 4-benzyloxydiphenylamine and 89.2g. of p-chlorobenzoyl chloride according to the procedure of Example 12. The product was recrystallized from benzene-hexane to give 4'-benzyloxy-4-chloro-N-phenylbenzanilide, m.p. 132°–136°C.

b. 4'-Hydroxy-4-chloro-N-phenylbenzanilide [V; R is $C_6H_5$, Ar is -$C_6H_4$-(p), R' is H, n is O, Ar' is $C_6H_4Cl$-4] was prepared by hydrogenolysis of 4'-benzyloxy-4-chloro-N-phenylbenzanilide according to the procedure of Example 51(b). The product was recrystallized from isopropyl alcohol to give 4'-hydroxy-4-chloro-N-phenylbenzanilide, m.p. 224°–225°C.

c. 4'-(3-Dimethylaminopropoxy)-4-chloro-N-phenylbenzanilide [IA; R is $C_6H_5$, Ar is -$C_6H_4$-(p), Y is $CH_2CH_2CH_2$, N=Z is $N(CH_3)_2$, n is O, Ar' is $C_6H_4Cl$-4] was prepared from 9.69 g. of 4'-hydroxy-4-chloro-N-phenylbenzanilide and 7.3 g. of 3-dimethylaminopropyl chloride in the presence of sodium methoxide according to the procedure of Example 1. The product was recrystallized from benzene-hexane to give 4'-(3-dimethylaminopropoxy)-4-chloro-N-phenylbenzanilide, colorless solid, m.p. 81.5°–85.5°C.

EXAMPLE 53 a. 4'-Benzyloxy-N-phenylbenzanilide [V; R is $C_6H_5$, Ar is -$C_6H_4$-(p), R' is $CH_2C_6H_5$, n is O, Ar' is $C_6H_5$] was prepared from 137.5 g. of 4-benzyloxydiphenylamine and 89.4 ml. of benzoyl chloride according to the procedure of Example 12. The product was recrystallized from benzene-hexane to give 4'-benzyloxy-N-phenylbenzanilide, m.p. 141°–143°C.

b. 4'-Hydroxy-N-phenylbenzanilide [V; R is $C_6H_5$, Ar is -$C_6H_4$-(p), R' is H, n is O, Ar' is $C_6H_5$] was prepared by hydrogenolysis of 4'-benzyloxy-N-phenylbenzanilide according to the procedure of Example 51(b). The product was recrystallized from isopropyl alcohol to give 4'-hydroxy-N-phenylbenzanilide, brown solid, m.p. 257°–260°C.

c. 4'-[2-(1-Piperidyl)ethoxy]-N-phenylbenzanilide [IA; R is $C_6H_5$, Ar is -$C_6H_4$-(p), Y is $CH_2CH_2$, N=Z is $N(CH_2)_5$, n is O, Ar' is $C_6H_5$] was prepared from 11.5 g. of 4'-hydroxy-N-phenylbenzanilide and 2-(1-piperidyl)ethyl chloride in the presence of sodium methoxide according to the procedure of Example 1. The product was recrystallized from benzene-hexane to give 4'-]2-(1-piperidyl)ethoxy]-N-phenylbenzanilide, colorless solid, m.p. 78.5°–82.5°C.; cyclohexanesulfamic acid salt form, m.p. 151.5°–157.5°C.

EXAMPLE 54

4'-[2-(4-Morpholinyl)ethoxy]-N-phenylbenzanilide [IA; R is $C_6H_5$, Ar is -$C_6H_4$-(p), Y is $CH_2CH_2$, N=Z is $N(CH_2)_4O$, n is O, Ar' is $C_6H_5$] was prepared from 10.1 g. of 4'-hydroxy-N-phenylbenzanilide and 2-(4-morpholinyl)ethyl chloride in the presence of sodium methoxide according to the procedure of Example 1. The product was recrystallized from benzene-hexane to give 4'-[2-(4-morpholinyl)ethoxy]-N-phenylbenzanilide, tan solid, m.p. 81.5°–84.5°C.

EXAMPLE 55

4'-(2-Diethylaminoethoxy)-4-amino-N-phenylbenzanilide [IA; R is $C_6H_5$, Ar is -$C_6H_4$-(p), Y is $CH_2CH_2$, N=Z is $N(C_2H_5)_2$, n is O, Ar' is $C_6H_4NH_2$-4].

A solution of 4.69 g. of 4'-(2diethylaminoethoxy)-4-nitro-N-phenylbenzanilide (Example 20) in 300 ml. of ethanol was hydrogenated in the presence of 1 g. of palladium-on-carbon catalyst. The catalyst was removed by filtration, the filtrate evaporated to remove the solvent, and the residue recrystallized from isopropyl alcohol-ether and ethanol-ether to give 4'-(2-diethylaminoethoxy)-4-amino-N-phenylbenzanilide, yellow solid, m.p. 174.5°–178.5°C.

EXAMPLE 56

4-(2-Dimethylaminoethoxy)-N-(4-aminobenzyl)diphenylamine [IIA; R is $C_6H_5$, Ar is -$C_6H_4$-(p), Y is $CH_2CH_2$, N=Z is $N(CH_3)_2$, m is 1, Ar' is $C_6H_4NH_2$-4] was prepared by catalytic hydrogenation of 4-(2-dimethylaminoethoxy)-N-(4-nitrobenzyl)diphenylamine (Example 44) according to the procedure of Examples 55. The product was obtained in the form of its tricyclohexanesulfonate salt, orange solid, m.p. 130°–137°C. (from acetone-ether).

EXAMPLE 57 a. 4-[2-(N-Benzyl-N-methylamino)ethoxy]diphenylamine [IV; R is $C_6H_5$, Ar is -$C_6H_4$-(p), Y is $CH_2CH_2$, N=Z is $N(CH_3)CH_2C_6H_5$] was prepared from 55.5 g. of p-anilinophenol and 2-(N-benzyl-N-methylamino)ethyl chloride in the presence of sodium methoxide according to the procedure of Example 1. The free base form of the product was distilled at 180°–230°C. (0.05 mm.) and treated with alcoholic hydrogen chloride to give 4-[2-(N-benzyl-N-methylamino)ethoxy]diphenylamine in its hydrochloride salt form, m.p. 132°–136°C. (from acetone).

b. 4'-[2-(N-Benzyl-N-methylamino)ethoxy]-N-phenylbenzanilide [IA; R is $C_6H_5$, Ar is -$C_6H_4$-(p), Y is $CH_2CH_2$, N=Z is $N(CH_3)CH_2C_6H_5$, $n$ is O, Ar' is $C_6H_5$] was prepared from 48.6 g. of 4-[2-(N-benzyl-N-methylamino)ethoxy]diphenylamine and 19.8 ml. of benzoyl chloride according to the procedure of Example 12.

The product was used directly in the following hydrogenolysis procedure.

c. 4'-(2-Methylaminoethoxy)-N-phenylbenzanilide [IA; R is $C_6H_5$, Ar is -$C_6H_4$-(p), Y is $CH_2CH_2$, N=Z is $NHCH_3$, $n$ is O, Ar' is $C_6H_5$] was prepared by hydrogenolysis of a benzene solution of 53.3 g. of 4'-[2-(N-benzyl-N-methylamino)ethoxy]-N-phenylbenzanilide in the presence of 4 g. of palladium-on-carbon catalyst, and was obtained in the form of its hydrochloride salt, colorless solid, m.p. 196.5°–202°C.

EXAMPLE 58

4-(2-Methylaminoethoxy)-N-benzyldiphenylamine [IIA; R is $C_6H_5$, Ar is -$C_6H_4$-(p), Y is $CH_2CH_2$, N=Z is $NHCH_3$, $m$ is 1, Ar' is $C_6H_5$] was prepared by diborane reduction of 
4'-(2-methylaminoethoxy)-N-phenylbenzanilide (Example 57c) according to the procedure of Example 42, and was obtained in the form of its hydrochloride salt, colorless solid, m.p. 177°–182° C. (from ethanol).

EXAMPLE 59 a. 4-Benzyloxy-N-benzyldiphenylamine [VI; R is $C_6H_5$, Ar is -$C_6H_4$-(p), R' is $CH_2C_6H_5$, $m$ is 1, Ar' is $C_6H_5$].

A mixture of 55 g. of 4-benzyloxydiphenylamine, 27.4 ml. of benzyl chloride and 33.1 g. of potassium carbonate was heated at 200°C. for 2½ hours. The reaction mixture was steam distilled to a clear distillate and extracted with hexane. The hexane extracts were diluted with chloroform, dried and concentrated. The residue was crystallized from ethanol to give 4-benzyloxy-N-benzyldiphenylamine, m.p. 104°–109°C.

b. 4-Hydroxy-N-benzyldiphenylamine [VI; R is $C_6H_5$, Ar is -$C_6H_4$-(p), R' is H, $m$ is 1, Ar' is $C_6H_5$] was prepared by hydrogenolysis of an ethanol solution of 4-benzyloxy-N-benzyldiphenylamine in the presence of palladium-on-carbon catalyst, and had the m.p. 122°–127°C. when recrystallized from benzene.

c. 4-(2-Diethylaminoethoxy)-N-benzyldiphenylamine [IIA; R is $C_6H_5$, Ar is -$C_6H_4$-(p), Y is $CH_2CH_2$, N=Z is $N(C_2H_5)_2$, $m$ is 1, Ar' is $C_6H_5$] was prepared from 4-hydroxy-N-benzyldiphenylamine and 2-diethylaminoethyl chloride in the presence of sodium methoxide according to the procedure of Example 1. There was thus obtained 4-(2-diethylaminoethoxy)-N-benzyldiphenylamine, b.p. 170°–190°C. (0.3 mm.); cyclohexanesulfamate salt form, colorless solid, m.p. 112°–115°C. (from acetone).

Similarly, the following compounds were obtained from 4-hydroxy-N-benzyldiphenylamine and the appropriate aminoalkyl halide:

EXAMPLE 60

4-[2-(1-Pyrrolidyl)ethoxy]-N-benzyldiphenylamine [IIA; R is $C_6H_5$, Ar is -$C_6H_4$-(p), Y is $CH_2CH_2$, N=Z is $N(CH_2)_4$, $m$ is 1, Ar' is $C_6H_5$], free base form, m.p. 59°–64°C. (from pentane); cyclohexanesulfamate salt form, colorless solid, m.p. 145.5°–147.5°C.

EXAMPLE 61

4-(2-Dimethylaminoethoxy)-N-benzyldiphenylamine [IIA; R is $C_6H_5$, Ar is -$C_6H_4$-(p), Y is $CH_2CH_2$, N=Z is $N(CH_3)_2$, $m$ is 1, Ar' is $C_6H_5$], free base form, b.p. 200°–208°C. (0.6 mm.); dicyclohexanesulfamate salt form, colorless solid, m.p. 115°–119°C. (from acetone-ether).

4-(2-Dimethylaminoethoxy)-N-benzyldiphenylamine (5.22 g.) was dissolved in 200 ml. of ether and 10 ml. of methanol and cooled in an ice-salt bath. Methyl bromide (12 ml.) was added, and the mixture was stirred one hour at ice-salt temperature and one hour at room temperature. The solid product which separated was collected and recrystallized from isopropyl alcohol-ether to give 4-(2-dimethylaminoethoxy)-N-benzyldiphenylamine in the form of its methobromide salt, grey solid, m.p. 171°–176°C.

EXAMPLE 62

4-(3-Dimethylaminopropoxy)-N-benzyldiphenylamine [IIA; R is $C_6H_5$, Ar is -$C_6H_4$-(p), Y is $CH_2CH_2CH_2$, N=Z is $N(CH_3)_2$, $m$ is 1, Ar' is $C_6H_5$], light brown solid, m.p. 74.5°–78.5°C. (from hexane).

EXAMPLE 63

4-[2-(1-Piperidyl)ethoxy]-N-benzyldiphenylamine [IIA; R is $C_6H_5$, Ar is -$C_6H_4$-(p), Y is $CH_2CH_2$, N=Z is $N(CH_2)_5$, $m$ is 1, Ar' is $C_6H_5$], b.p. 210°–225°C. (0.04 mm.), light tan solid, m.p. 78.5°–79.5°C. (from isopropyl alcohol).

EXAMPLE 64

4-[2-(4-Morpholinyl)ethoxy]-N-benzyldiphenylamine [IIA; R is $C_6H_5$, Ar is -$C_6H_4$-(p), Y is $CH_2CH_2$, N=Z is $N(CH_2)_4O$, $m$ is 1, Ar' is $C_6H_5$], b.p. 220°–230°C. (0.01 mm.), colorless solid, m.p. 67.5°–71.5°C. (from benzene-hexane).

EXAMPLE 65 a. 4-Benzyloxy-N-(4-methoxybenzyl)diphenylamine [VI; R is $C_6H_5$, Ar is -$C_6H_4$-(p), R' is $CH_2C_6H_5$, $m$ is 1, Ar' is $C_6H_4OCH_3$-4] was prepared by diborane reduction of 4'-benzyloxy-4-methoxy-N-phenylbenzanilide (Example 51a) according to the procedure of Example 42, and was obtained in the form of a colorless solid, m.p. 62°–65°C. when recrystallized from ethanol.

b. 4-Hydroxy-N-(4-methoxybenzyl)diphenylamine [VI; R is $C_6H_5$, Ar is -$C_6H_4$-(p), R' is H, $m$ is 1, Ar' is $C_6H_4OCH_3$-4] was prepared by hydrogenolysis of 4-benzyloxy-N-(4-methoxybenzyl)diphenylamine in the presence of palladium-on-carbon catalyst, and was obtained in the form of a colorless solid, m.p. 76.5°–78°C. when recrystallized from benzene-hexane.

c. 4-(2-Diethylaminoethoxy)-N-(4-methoxybenzyl)-diphenylamine [IIA; R is C$_6$H$_5$, Ar is -C$_6$H$_4$-(p), Y is CH$_2$CH$_2$, N=Z is N(C$_2$H$_5$)$_2$, m is 1, Ar' is C$_6$H$_4$OCH$_3$-4] was prepared from 4-hydroxy-N-(4-methoxybenzyl)diphenylamine and 2-diethylaminoethyl chloride in the presence of sodium methoxide according to the procedure of Example 1, and was obtained in the form of its cyclohexanesulfamate salt, light tan solid, m.p. 105°–107°C. (from ethyl acetate-ether).

EXAMPLE 66 a. N-(2-Pyridyl)-4-benzyloxyaniline [III; R is 2-pyridyl, Ar is -C$_6$H$_4$-(p), R' is CH$_2$C$_6$H$_5$].

A mixture of 19.93 g. of 4-benzyloxyaniline and 4.77 ml. of 2-bromopyridine was stirred and gradually heated over a period of 2½ hours to 150°C. The mixture was held at 160°C. for 1 hour and at 130°C. for one and three-quarters hours, and then steam distilled. The residue was filtered and the filtrate made alkaline. The combined solid products were recrystallized from cyclohexane to give N-(2-pyridyl)-4-benzyloxyaniline, tan prisms, m.p. 110°–111.5°C.

b. N-Benzyl-N-(2-pyridyl)-4-benzyloxyaniline [VI; R is 2-pyridyl, Ar is -C$_6$H$_4$-(p), R' is CH$_2$C$_6$H$_5$, m is 1, Ar' is C$_6$H$_5$].

A solution of 8.09 g. of N-(2-pyridyl)-4-benzyloxyaniline in 120 ml. of toluene was distilled until 15–25 ml. was collected in order to remove moisture, nitrogen was introduced into the system, and 4.60 g. of potassium tertiary-butoxide was added in portions over a 1–1.5 minute period. The mixture was stirred at reflux for 1 hour and 4.02 ml. of benzyl chloride was then added dropwise to the stirred suspension. The reaction mixture was stirred at reflux for 16 hours, then cooled and 50 ml. of water added. The layers were separated and the aqueous layer washed with benzene. The organic extracts were combined, washed with saturated sodium chloride solution, dried over anhydrous magnesium sulfate and concentrated to dryness. The residue was recrystallized from cyclohexane to give 5.6 g. of N-benzyl-N-(2-pyridyl)-4-benzyloxyaniline, m.p. 98.5°–100°C.

c. 4-Hydroxy-N-benzyl-N-(2-pyridyl)aniline [VI; R is 2-pyridyl, Ar is -C$_6$H$_4$-(p), R' is H, m is 1, Ar' is C$_6$H$_5$] was prepared by hydrogenolysis of N-benzyl-N-(2-pyridyl)-4-benzyloxyaniline in the presence of palladium-on-carbon catalyst, and obtained as a crystalline solid, m.p. 171°–173°C. when recrystallized from benzene.

d. 4-(2-Dimethylaminoethoxy)-N-benzyl-N-(2-pyridyl)aniline [IIA; R is 2-pyridyl, Ar is -C$_6$H$_4$-(p), Y is CH$_2$CH$_2$, N=Z is N(CH$_3$)$_2$, m is 1, Ar' is C$_6$H$_5$] was prepared from 4-hydroxy-N-benzyl-N-(2-pyridyl)aniline and 2-dimethylaminoethyl chloride according to the procedure of Example 1, and was obtained in the form of cream-colored crystals, m.p. 50.5°–53°C. (from ether).

EXAMPLE 67 a. 4-Benzyloxy-N-phenylbenzanilide [VII; R is C$_6$H$_5$, Ar is C$_6$H$_5$, n is O, Ar' is -C$_6$H$_4$-(p)] was prepared from 37.2 g. of diphenylamine, 0.24 mole of 4-benzyloxybenzoyl chloride and 25.3 g. of sodium carbonate in toluene solution, 20 hours at reflux, and was obtained as light tan prisms, m.p. 119°–121°C. when recrystallized from cyclohexane.

b. 4-Hydroxy-N-phenylbenzanilide [VIII: R is C$_6$H$_5$, Ar is C$_6$H$_5$, n is O, Ar' is -C$_6$H$_4$-(p)] was prepared by hydrogenolysis of 4-benzyloxy-N-phenylbenzanilide in the presence of palladium-on-carbon catalyst, and was obtained as colorless prisms, m.p. 192.3°–194.4°C. (from isopropyl alcohol).

c. 4-[2-(1-Pyrrolidyl)ethoxy]-N-phenylbenzanilide [IB; R is C$_6$H$_5$, Ar is C$_6$H$_5$, n is O, Ar' is -C$_6$H$_4$-(p), Y is CH$_2$CH$_2$, N=Z is N(CH$_2$)$_4$] was prepared from 4-hydroxy-N-phenylbenzanilide and 2-(1-pyrrolidyl)ethyl chloride according to the procedure of Example 1, and was obtained as colorless prisms, m.p. 80°–82°C. (from ether).

Similarly, the following were prepared from 4-hydroxy-N-phenylbenzanilide and the appropriate aminoalkyl halide:

EXAMPLE 68

4-(2-Dimethylaminoethoxy)-N-phenylbenzanilide [IB; R is C$_6$H$_5$, Ar is C$_6$H$_5$, n is O, Ar' is -C$_6$H$_4$-(p), Y is CH$_2$CH$_2$, N=Z is N(CH$_3$)$_2$], colorless prisms, m.p. 89°–90°C. (from isopropyl alcohol-ether).

EXAMPLE 69

4-(3-Dimethylaminopropoxy)-N-phenylbenzanilide [IB; R is C$_6$H$_5$, Ar is C$_6$H$_5$, n is O, Ar' is -C$_6$H$_4$-(p), Y is CH$_2$CH$_2$CH$_2$, N=Z is N(CH$_3$)$_2$], light tan prisms, m.p. 112°–112.5°C. (from ether).

EXAMPLE 70

4-[2-(1-Piperidyl)ethoxy]-N-phenylbenzanilide [IB; R is C$_6$H$_5$, Ar is C$_6$H$_5$, n is O, Ar' is -C$_6$H$_4$-(p), Y is CH$_2$CH$_2$, N=Z is N(CH$_2$)$_5$], light tan solid, m.p. 80°–82.5°C. (from acetone-methanol-ether).

EXAMPLE 71

N-[4-(2-Dimethylaminoethoxy)benzyl]diphenylamine [IIB; R is C$_6$H$_5$, Ar is C$_6$H$_5$, m is 1, Ar' is -C$_6$H$_4$-(p), Y is Ch$_2$CH$_2$, N=Z is N(CH$_3$)$_2$] was prepared by diborane reduction of 4-(2-dimethylaminoethoxy)-N-phenylbenzanilide (Example 68) according to the procedure of Example 42, and was obtained as the free base, m.p. 81°–82.5°C. (from cyclohexane), and in the form of its hydrochloride salt, colorless prisms, m.p. 167°–169°C. (from acetone-isopropyl alcohol-ether).

EXAMPLE 72

N-{4-[2-(1-Pyrrolidyl)ethoxy]benzyl}diphenylamine [IIB; R is C$_6$H$_5$, Ar is C$_6$H$_5$, m is 1, Ar' is -C$_6$H$_4$-(p), Y is CH$_2$CH$_2$, N=Z is N(CH$_2$)$_4$] was prepared by diborane reduction of 4-[2-(1-pryrrolidyl)ethoxy]-N-phenylbenzanilide (Example 67c), and was obtained in the form of its hydrochloride salt, colorless prisms, m.p. 177°–179°C. (from acetone-methanol-ether).

In testing the compounds of the invention for hypocholesteremic activity, according to standard procedure mature male Sprague-Dawley strain rats, weighing 165 to 185 grams, were maintained on a fixed diet. On days one through seven, aside from the unmedicated control groups, the rats were given varying doses of the test compound by intubation as a suspension in 10% aqueous gum tragacanth. On the eight day blood was taken by cardiac puncture, permitted to clot, centrifuged and the serum drawn off for cholesterol determination. Cholesterol content was determined by the Turner et al. (loc. cit.) procedure. Activity is reported in terms of the dose level in mg./kg./day causing a significant decrease in serum cholesterol levels or as an ED$_{33}$, which is an estimate of the dose in mg./kg./day required to lower the serum cholesterol level by 33 percent. When tested by the foregoing procedure, the compounds of the invention were found to show hypocholesteremic activity in a dose level of about 100 mg./kg./day.

I claim:

1. A compound of the formula

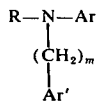

wherein R is lower-alkoxyphenyl; m is an integer from 1 to 4; Ar and Ar' are phenyl, Ar being substituted in the meta or para position by the grouping -O-Y-N=Z, wherein Y is lower -alkylene of at least two and not more than five carbon atoms, and -N=Z is NH$_2$; alkylamino; cycloalkylamino in which the cycloalkyl has from 5 to 6 ring members and a total of from five to nine carbon atoms and is selected from the group consisting of unsubstituted cycloalkyl and alkylsubstituted cycloalkyl; dialkylamino; dicycloalkylamino in which the cycloalkyl has from 5 to 6 ring members and a total of from five to nine carbon atoms and is selected from the group consisting of unsubstituted cycloalkyl and alkyl-substituted cycloalkyl; N-(cycloalkyl) alkylamino in which the cycloalkyl has from 5 to 6 ring members and a total of from five to nine carbon atoms and is selected from the group consisting of unsubstituted cycloalkyl and alkyl-substituted cycloalkyl; polymethylenimino having from 5 to 7 ring members and a total of from four to nine carbon atoms selected from the group consisting of unsubstituted polymethylenimino and alkyl-substituted polymethylenimino; 4-morpholinyl; 1-piperazinyl; 4-alkyl-1-piperazinyl; 4-phenyl-1-piperazinyl; di(phenylalkyl)amino; or N-(phenylalkyl) alkylamino, alkyl in each instance having from one to six carbon atoms; and wherein the phenyl rings of Ar and Ar' can be further substituted by from one to three groups selected from the group consisting of lower-alkyl, lower-alkoxy, halogen, nitro and amino.

2. 4-[2-(1-Pyrrolidyl)ethoxy]-4'-methoxy-N-benzyl-diphenylamine, a compound according to claim 1, wherein m is 1, Ar' is phenyl, Y is ethylene, and N=Z is 1-pyrrolidyl.

3. A compound of the formula

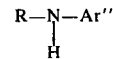

wherein R is lower-alkoxyphenyl; and Ar'' is phenyl substituted in the meta or para position by the grouping -O-Y-N=Z, wherein Y is lower-alkylene of at least two and not more than five carbon atoms, and -N=Z is NH$_2$; alkylamino; cycloalkylamino in which the cycloalkyl has from 5 to 6 ring members and a total of from five to nine carbon atoms and is selected from the group consisting of unsubstituted cycloalkyl and alkyl-substituted cycloalkyl; dialkylamino; dicycloalkylamino in which the cycloalkyl has from 5 to 6 ring members and a total of from five to nine carbon atoms and is selected from the group consisting of unsubstituted cycloalkyl and alkyl-substituted cycloalkyl; N-(cycloalkyl)alkylamino in which the cycloalkyl has from 5 to 6 ring members and a total of from five to nine carbon atoms and is selected from the group consisting of unsubstituted cycloalkyl and alkyl-substituted cycloalkyl; polymethylenimino having from 5 to 7 ring members and a total of from four to nine carbon atoms selected from the group consisting of unsubstituted polymethylenimino and alkyl-substituted polymethylenimino; 4-morpholinyl; 1-piperazinyl; 4-alkyl-1-piperizinyl; 4-phenyl-1-piperazinyl; di(phenylalkyl)amino; or N-(phenylalkyl)alkylamino, alkyl in each instance having from one to six carbon atoms.

4. A compound according to claim 3 wherein the grouping -O-Y-N=Z is in the para position of the group Ar''.

5. 4-[2-(1-Pyrrolidyl)ethoxy]-4'-methoxydiphenylamine, a compound according to claim 4, wherein R is 4-methoxyphenyl, Y is ethylene, and N=Z is 1-pyrrolidyl.

* * * * *

UNITED STATES PATENT AND TRADEMARK OFFICE
CERTIFICATE OF CORRECTION

PATENT NO. : 3,960,886
DATED : June 1, 1976
INVENTOR(S) : John W. Schulenberg

It is certified that error appears in the above—identified patent and that said Letters Patent are hereby corrected as shown below:

Column 5, line 49, "Example" should read --capable--.

Column 26, line 32, Claim 3, "piperizinyl" should read --piperazinyl--.

Signed and Sealed this

Fourteenth Day of September 1976

[SEAL]

*Attest:*

RUTH C. MASON
*Attesting Officer*

C. MARSHALL DANN
*Commissioner of Patents and Trademarks*